(12) United States Patent
Krüger et al.

(10) Patent No.: US 9,359,306 B2
(45) Date of Patent: Jun. 7, 2016

(54) PROCESS FOR PREPARING PAN-CDK INHIBITORS OF THE FORMULA (I), AND INTERMEDIATES IN THE PREPARATION

(75) Inventors: Joachim Krüger, Düsseldorf (DE); Jörg Gries, Haan (DE); Kai Lovis, Wuppertal (DE); Jorma Haβfeld, Düsseldorf (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 13/824,160

(22) PCT Filed: Sep. 20, 2011

(86) PCT No.: PCT/EP2011/066295
§ 371 (c)(1),
(2), (4) Date: Jun. 4, 2013

(87) PCT Pub. No.: WO2012/038411
PCT Pub. Date: Mar. 29, 2012

(65) Prior Publication Data
US 2013/0245261 A1 Sep. 19, 2013

(30) Foreign Application Priority Data
Sep. 23, 2010 (DE) .......................... 10 2010 046 720

(51) Int. Cl.
*C07D 239/47* (2006.01)
*C07C 69/76* (2006.01)
*C07C 309/29* (2006.01)
*C07C 381/10* (2006.01)

(52) U.S. Cl.
CPC .............. *C07D 239/47* (2013.01); *C07C 69/76* (2013.01); *C07C 309/29* (2013.01); *C07C 381/10* (2013.01)

(58) Field of Classification Search
CPC ..................................................... C07D 239/47
See application file for complete search history.

(56) References Cited

U.S. PATENT DOCUMENTS

2010/0076000 A1* 3/2010 Kruger et al. ................. 514/275

FOREIGN PATENT DOCUMENTS

WO  WO 2010046035 A1 * 4/2010

\* cited by examiner

*Primary Examiner* — Noble Jarrell
*Assistant Examiner* — John S Kenyon

(57) ABSTRACT

The invention relates to a novel process for the preparation of pan-CDK inhibitors of the formula (I), and intermediates of the preparation.

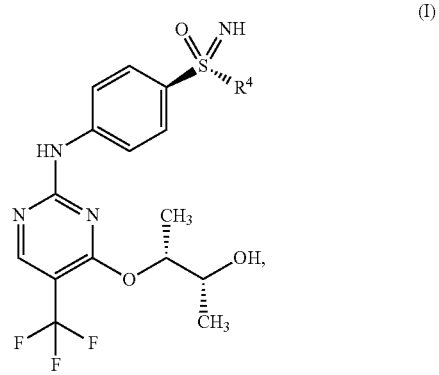

19 Claims, No Drawings

PROCESS FOR PREPARING PAN-CDK INHIBITORS OF THE FORMULA (I), AND INTERMEDIATES IN THE PREPARATION

The invention relates to a novel process for the preparation of pan-CDK inhibitors of the formula (I), and to intermediates of the preparation.

The novel process relates to compounds of the formula (I), in particular the compound (2R,3R)-3-{[2-{[4-(S-cyclopropylsulphonimidoyl)phenyl]amino}-5-(trifluoromethyl)pyrimidin-4-yl]oxy}butan-2-ol (compound A), which develop their anti-tumour activity via a cytotoxic mechanism.

A preparation process for a compound of the general formula (I) has now been found,

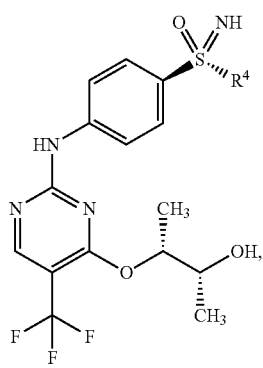

(I)

in which
$R^4$ is a $C_1$-$C_6$-alkyl group or a $C_3$-$C_7$-cycloalkyl ring, which is suitable for a scale-up and overcomes the disadvantages of the preparation processes of the prior art for this substance class.

This preparation process is particularly suitable for the compound A

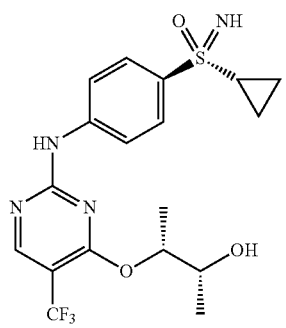

Compound A

The application is based on the following definitions:
$C_1$-$C_6$-alkyl

A $C_1$-$C_6$-alkyl group is to be understood in each case as meaning a straight-chain or branched alkyl radical, such as, for example, a methyl, ethyl, propyl, isopropyl, butyl, isobutyl, sec-butyl, tert-butyl, pentyl, isopentyl or a hexyl radical.
$C_3$-$C_7$-cycloalkyl A $C_3$-$C_7$-cycloalkyl ring is to be understood as meaning a cyclopropyl, cyclobutyl, cyclopentyl, cyclohexyl or a cycloheptyl ring.

Compounds of the general formula (I), in particular also the compound A and processes for their preparation are disclosed in WO2010/046035A1, the disclosure of which forms the closest prior art.

The process according to WO2010/046035A1 is a 10-stage convergent process with an overall yield for the longest sequence of ca. 7%.

The process according to WO2010/046035A1 involves at least one of the following steps:

a) Oxidation of a nitrophenyl-sulphide of the formula (I-1) to give the nitrophenyl-sulphoxide of the formula (I-2).

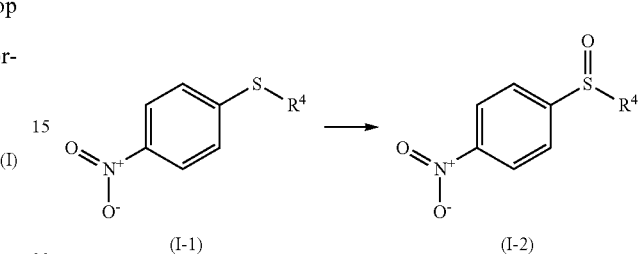

b₁) Direct imination of the nitrophenyl-sulphoxide of the formula (I-2) to give a trifluoroacetate-protected nitrophenyl-sulphoximine of the formula (I-3).

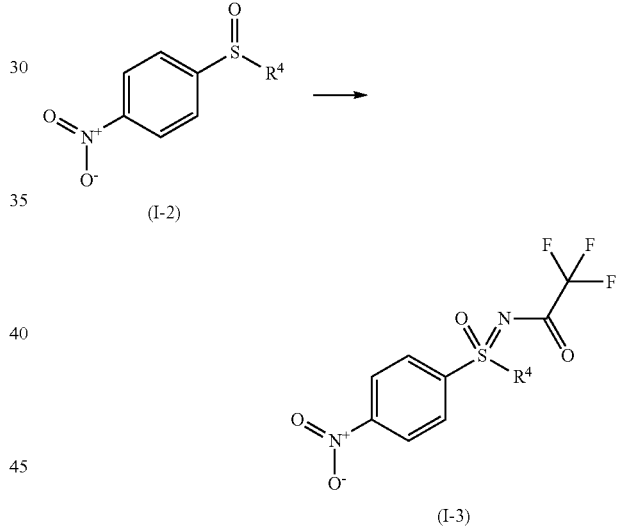

b₂) Imination of the nitrophenyl-sulphoxide of the formula (I-2) to give a nitrophenyl-sulphoximine of the formula (I-11) and subsequent insertion of the protective group to give a trifluoroacetate-protected nitrophenyl-sulphoximine of the formula (I-3).

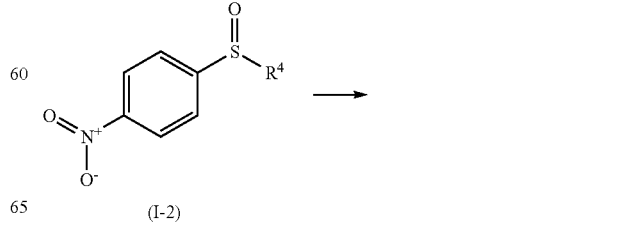

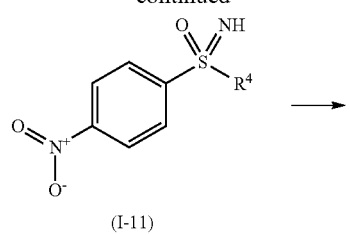

(I-11)

c) Reduction of the compound of the formula (I-3) to give a compound of the formula (I-4)

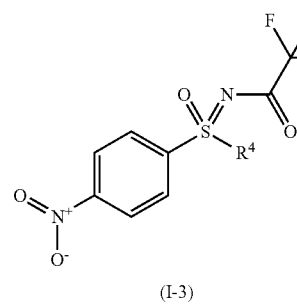

(I-3)

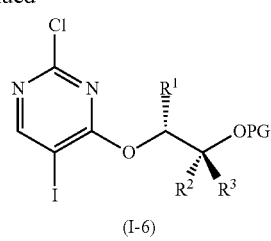

(I-6)

e) Preparation of the protected 5-CF$_3$ intermediate (I-7).

f) Coupling of the compounds of the formula (I-7) and (I-4) to give a doubly protected anilinopyrimidine of the formula (I-8).

d) Functionalization of the 4-position of 2,4-dichloro-5-iodopyrimidine by reaction with a mono-protected diol of the formula (I-5) to form a protected hydroxyalkoxypyrimidine of the formula (I-6).

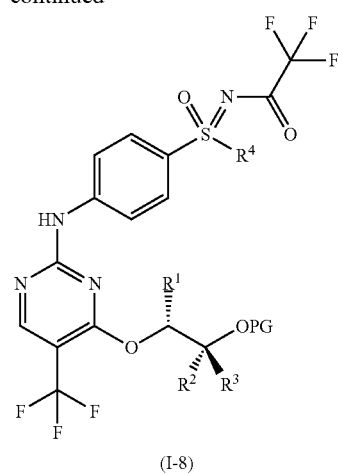

(I-8)

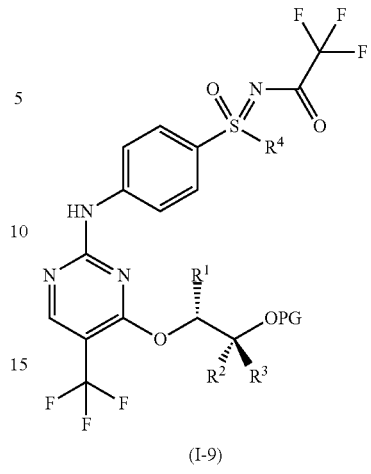

(I-9)

g) Cleaving off of the protective group (PG) to form a singly protected anilinopyrimidine (I-9).

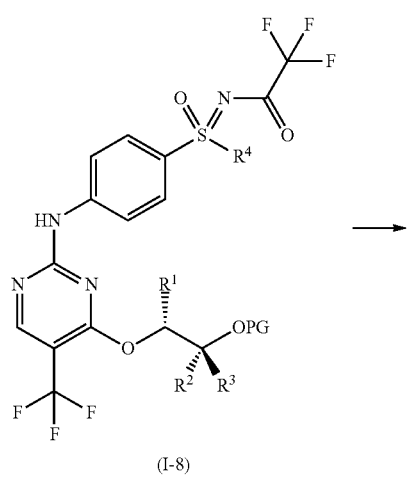

(I-8)

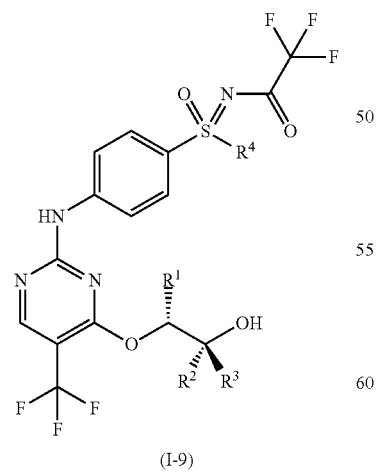

(I-9)

h) Cleaving off of the protective group on the sulphoximine to form compounds of the formula (I).

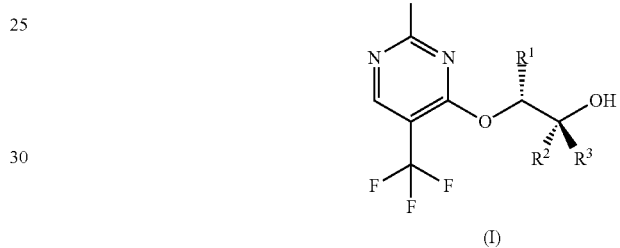

(I)

where in WO2010/046035A1
$R^1$ is a methyl, ethyl, propyl or isopropyl group, and
$R^2$ and $R^3$ independently of one another are hydrogen, a methyl or ethyl group, and
$R^4$ is a $C_1$-$C_6$-alkyl group or a $C_3$-$C_7$-cycloalkyl ring.

The diastereomers of the formula I were separated by means of preparative chromatography. The experimental details are given in WO2010/046035A1.

For the compound A, in WO2010/046035A1, the following conditions were disclosed for the individual synthesis steps:

Preparation of the Intermediates 1-cyclopropylsulphanyl-4-nitrobenzene (I-1-A)

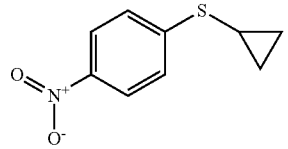 [SMILES: O=[N+]([O-])c1ccc(SC2CC2)cc1]

Cyclopropanethiol in THF/diethyl ether was admixed in portions with sodium hydride and stirred at room temperature. 1-Fluoro-4-nitrobenzene was then added in portions. The mixture was stirred for 2 hours at 40° C. After cooling, the mixture was added to water and extracted with benzene (3×). The combined organic phases were concentrated by evaporation and the residue was purified by chromatography (hexane/acetic ester 95:5). (Yield: 61%).

(RS)-1-cyclopropanesulphinyl-4-nitrobenzene
(I-2-A)

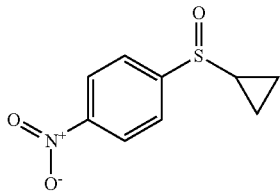 [SMILES: O=[N+]([O-])c1ccc(S(=O)C2CC2)cc1]

1-Cyclopropylsulphanyl-4-nitrobenzene in acetonitrile was admixed with iron(III) chloride and stirred at room temperature. Periodic acid was then added in portions. The mixture was stirred for 30 minutes and then added, with stirring, to a cooled, saturated sodium thiosulphate solution. Extraction was carried out with acetic ester (2×). The combined organic phases were dried ($Na_2SO_4$), filtered and concentrated by evaporation. The residue obtained was purified by means of chromatography (hexane/acetic ester 1:1) (yield: 76%).

(RS)—S-cyclopropyl-S-(4-nitrophenyl)-N-(trifluoroacetyl)sulphoximide (I-3-A)

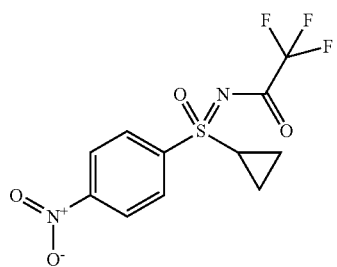 [SMILES: O=C(N=S(=O)(c1ccc([N+](=O)[O-])cc1)C1CC1)C(F)(F)F]

A suspension of (RS)-1-cyclopropanesulphinyl-4-nitrobenzene, trifluoroacetamide, iodobenzene diacetate and magnesium oxide in DCM was admixed, under argon, with rhodium(II) acetate dimer and stirred overnight at room temperature. The mixture was filtered off with suction over Celite and concentrated by evaporation. The remaining residue was purified by means of chromatography (hexane/acetic ester 2:1) (yield: 78%).

(RS)—S-(4-aminophenyl)-S-cyclopropyl-N-(trifluoroacetyl)sulphoximide (I-4-A)

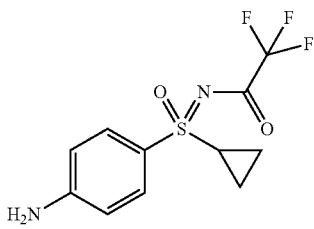 [SMILES: Nc1ccc(S(=O)(=NC(=O)C(F)(F)F)C2CC2)cc1]

A solution of (RS)—S-cyclopropyl-S-(4-nitrophenyl)-N-(trifluoroacetyl)sulphoximide in ethanol and THF was admixed with palladium on carbon and hydrogenated for 1 hour under atmospheric pressure at 25° C. Palladium on carbon was added again and the mixture was hydrogenated for a further 4.5 hours at atmospheric pressure. The mixture was filtered, the filtrate was again admixed with palladium on carbon and finally hydrogenated for 45 minutes. The mixture was filtered and concentrated by evaporation (yield: 93%).

(2R,3R)-3-benzyloxybutan-2-ol (I-5-A)

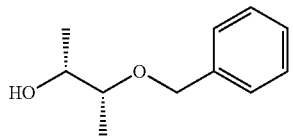

A solution of (2R,3R)-butane-2,3-diol in THF was admixed at room temperature with potassium tert-butylate and the mixture was refluxed for 15 minutes. The mixture was cooled to ca. 50° C. and admixed with benzyl bromide. The mixture was refluxed for 3 hours, then stirred overnight at room temperature. The mixture was diluted with acetic ester and sodium chloride solution and then washed with 1 N hydrogen chloride solution (1×) and sodium chloride solution (2×). The organic phase was dried ($Na_2SO_4$), filtered and concentrated by evaporation. The residue obtained was purified by means of chromatography (hexane/acetic ester 1:1) (yield: 43%).

4-((1R,2R)-2-benzyloxy-1-methylpropoxy)-2-chloro-5-iodopyrimidine (I-6-A)

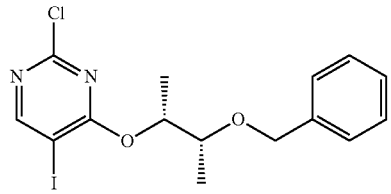 [SMILES: C[C@@H](OCc1ccccc1)[C@@H](C)Oc1nc(Cl)ncc1I]

(2R,3R)-3-Benzyloxybutan-2-ol in diethyl ether were admixed with sodium hydride in portions at 0° C. with stirring. After 10 minutes, the ice bath was removed and the mixture was stirred for a further 3 minutes at room temperature. The suspension formed was added, at 0° C., to a solution of 2,4-dichloro-5-iodopyrimidine. The mixture was stirred for 4 hours at 40° C. and then admixed with dilute sodium chloride solution. The mixture was extracted with acetic ester (2×). The combined organic phases were dried ($Na_2SO_4$), filtered and concentrated by evaporation. The resulting residue was purified by means of chromatography (hexane/acetic ester 4:1) (yield: 41%).

4-((1R,2R)-2-benzyloxy-1-methylpropoxy)-2-chloro-5-trifluoromethylpyrimidine (I-7-A)

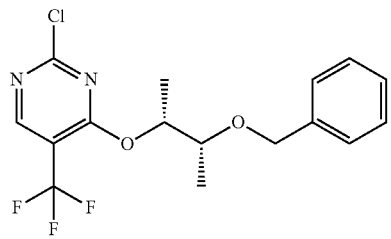 [SMILES: C[C@@H](OCc1ccccc1)[C@@H](C)Oc1nc(Cl)ncc1C(F)(F)F]

A solution of 4-((1R,2R)-2-benzyloxy-1-methylpropoxy)-2-chloro-5-iodopyrimidine in NMP and THF was admixed at room temperature with stirring with copper(I) iodide, potassium fluoride and (trifluoromethyl)trimethylsilane. The mixture was stirred for 5.5 hours at 80° C. After cooling, the mixture was added to dilute sodium chloride solution and extracted with acetic ester (2×). The combined organic phases were dried ($Na_2SO_4$), filtered and concentrated by evaporation. The residue obtained was purified by means of chromatography (hexane/acetic ester 4:1) (yield: 54%).

(RS)—S-(4-{[4-{[(1R,2R)-2-(benzyloxy)-1-methylpropyl]oxy}-5-(trifluoromethyl)pyrimidin-2-yl]amino}phenyl)-S-cyclopropyl-N-(trifluoroacetyl)sulphoximide (I-8-A)

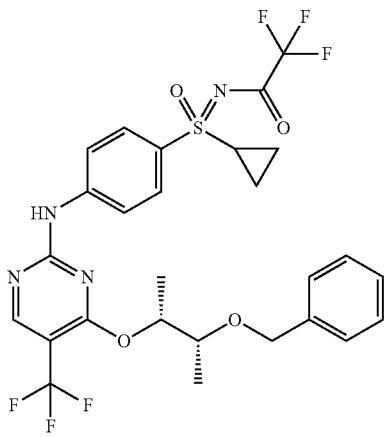 [SMILES: C[C@@H](OCc1ccccc1)[C@@H](C)Oc1nc(Nc2ccc(S(=O)(=NC(=O)C(F)(F)F)C3CC3)cc2)ncc1C(F)(F)F]

4-((1R,2R)-2-benzyloxy-1-methylpropoxy)-2-chloro-5-trifluoromethylpyrimidine and (RS)—S-(4-aminophenyl)-S-cyclopropyl-N-(trifluoroacetyl)sulphoximide in acetonitrile were admixed with a 4N solution of hydrogen chloride in dioxane and stirred for 5 hours at 80° C. After cooling, the mixture was diluted with acetic ester and washed with saturated sodium hydrogen carbonate solution and saturated sodium chloride solution, dried ($Na_2SO_4$), filtered and concentrated by evaporation. The resulting residue was purified by means of chromatography (hexane/acetic ester 4:1) (yield: 56%).

(RS)—S-cyclopropyl-S-(4-{[4-{[(1R,2R)-2-hydroxy-1-methylpropyl]oxy}-5-(trifluoromethyl)pyrimidin-2-yl]amino}phenyl)-N-(trifluoroacetyl)sulphoximide (I-9-A)

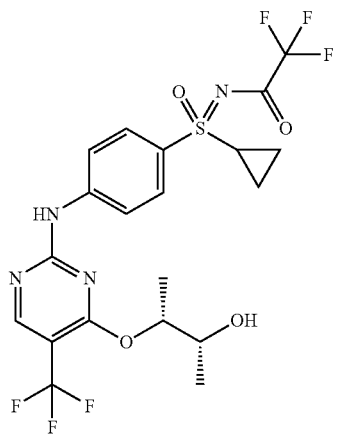 [SMILES: C[C@@H](O)[C@@H](C)Oc1nc(Nc2ccc(S(=O)(=NC(=O)C(F)(F)F)C3CC3)cc2)ncc1C(F)(F)F]

A solution of (RS)—S-(4-{[4-{[(1R,2R)-2-(benzyloxy)-1-methylpropyl]oxy}-5-(trifluoromethyl)pyrimidin-2-yl]amino}phenyl)-S-cyclopropyl-N-(trifluoroacetyl)sulphoximide in ethanol was admixed with palladium on carbon (10%) and hydrogenated under atmospheric pressure at room temperature. The mixture was filtered and concentrated by evaporation (yield: 79%).

Preparation of the Compound A (RS)—S-cyclopropyl-S-(4-{[4-{[(1R,2R)-2-hydroxy-1-methylpropyl]oxy}-5-(trifluoromethyl)pyrimidin-2-yl]amino}phenyl)-N-(trifluoroacetyl)sulphoximide in 35 ml of methanol were admixed with potassium carbonate and stirred for 1.5 hours at room temperature. The mixture was diluted with saturated sodium chloride solution and extracted with acetic ester (3×). The combined organic phases were dried ($Na_2SO_4$), filtered and concentrated by evaporation.

The diastereomer mixture was separated into the pure stereoisomers by means of preparative HPLC:
Column: Chiralpak IA 5μ 250×30 mm
Eluents: Hexane/ethanol 8:2
Flow: 40.0 ml/min
Detector: UV 254 nm
Temperature: Room temperature
Retention time: 10.8-13.4 min; stereoisomer 1
13.6-18.5 min; stereoisomer 2 (compound A)

This preparation of the compound of the formula (I) according to WO2010/046035A1 is unsuitable for a production process.

The most critical points are
- The majority of the intermediates are purified by means of chromatography. This is expensive and complex on a larger scale.
- The starting material (I-1) was prepared from cyclopropyl sulphide, which is not commercially available in large amounts.
- A racemic oxidation method was used for the preparation of (I-2). The stereoisomers therefore have to be separated by means of chromatography at the end of the synthesis. Since the separation only takes place at the end of the synthesis, the overall yield for the synthesis sequence is drastically reduced.
- In the preparation of (I-3), large amounts of rhodium(II) acetate dimer are used. This is expensive and the rhodium has to be removed so that there is no contamination in the active ingredient. Iodobenzene diacetate is unsuitable for a scale-up since it is not very available in large amounts and it is a potential explosive material.
- The alternative access to (I-3) via (I-2) and (I-2/3) is not easy to carry out for safety reasons since toxic and explosive substances such as sodium azide or o-mesitylenesulphonylhydroxylamine (MSH) are used.
- The synthesis of (I-5-A) is not selective since double alkylation also occurs. The yield is therefore only 43%.
- The sequence (I-6) to (I-7) is not convergent since the trifluoromethyl group is not already entrained in the pyrimidine building block. The yields of both steps is poor. Since the conversions proceed with the formation of many secondary components, it is additionally necessary to carry out chromatography, which is complex.
- Intermediate (I-8) is produced as an oil which can only be cleaned by means of chromatography. On an industrial scale, the oil can only be handled with difficulty and the storage stability is poor compared to a solid.

In stage (I-9), the diastereomers are separated by preparative methods. This is very complex and expensive. Moreover, much of the overall yield is lost since the separation is only carried out in the last synthesis stage.

These aspects have to be reworked and/or optimized in the course of expanding the synthesis to a multi-g or kg scale.

It was therefore an object of the present invention to provide a process for the pan-CDK inhibitors of the general formula (I), in particular for compound A, which does not have the aforementioned disadvantages.

I. Process Steps According to the Invention in the Preparation of Compounds of the General Formula (I)

The preparation process according to the invention is characterized by various advantageous preparation steps and also intermediates.

The process according to the invention for the preparation of compounds of the general formula (I) is characterized by at least one of the following steps:

I.a). Alkylation of 4-nitrothiophenol in the presence of potassium carbonate in N-methylpyrrolidinone (NMP) to give a nitrophenyl-sulphide of the formula (I-1)

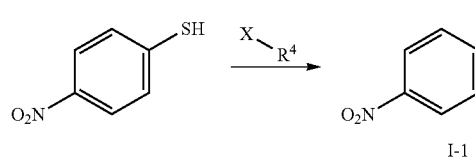

where X is Br, Cl, I, O—SO$_2$—CH$_3$ or O—SO$_2$-(4-methylphenyl)

I.b). Oxidative amination of the nitrophenyl-sulphide of the formula (I-1) to give a trifluoroacetate-protected nitrophenyl-sulphilimine of the formula (I-10)

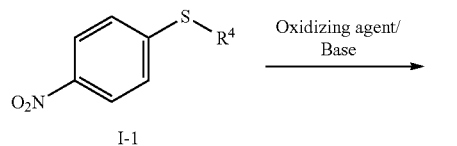

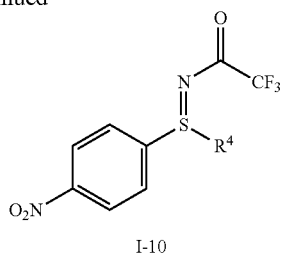

I.c). Oxidation of the trifluoroacetate-protected nitrophenyl-sulphilimine of the formula (I-10) to give a trifluoroacetate-protected nitrophenyl-sulphoximine of the formula (I-3) and subsequent deprotection to give a nitrophenyl-sulphoximine of the formula (I-11)

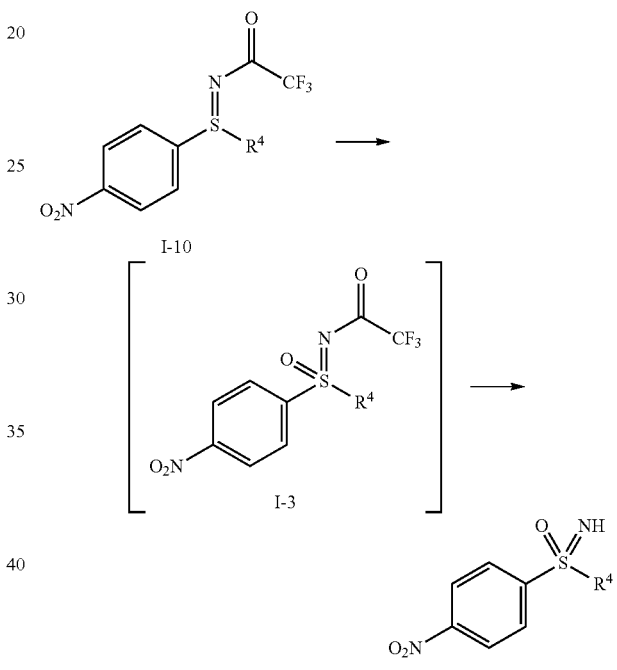

I.d). Racemate cleavage of a nitrophenyl-sulphoximine of the formula (I-11) with the help of (+)-di-O-p-toluoyl-D-tartaric acid

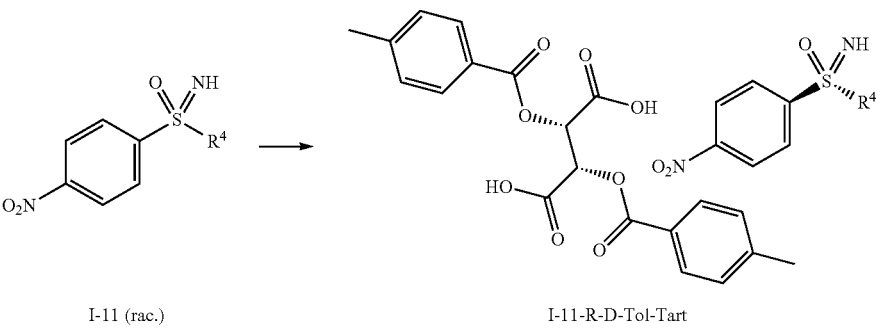

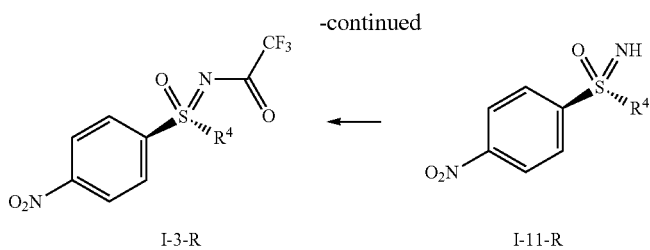

where the R enantiomer of the nitrophenyl-sulphoximine of the formula (I-11-R) is then released from the salts and the trifluoroacetate protective group is inserted again to form the R enantiomer of the trifluoroacetate-protected nitrophenyl-sulphoximine of the formula (I-3-R), I.e). Hydrogenation of trifluoroacetate-protected nitrophenyl-sulphoximines of the formula (I-3-R) to give trifluoroacetate-protected anilino-sulphoximines of the formula (I-4-R) with an iron-doped palladium catalyst

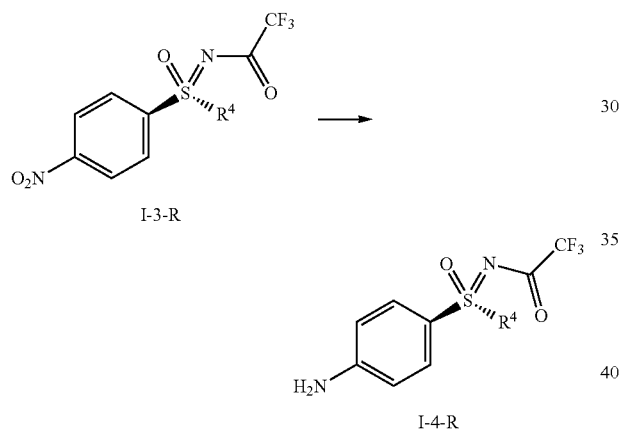

I.f). Preparation of (2R,3R)-3-(benzyloxy)butan-2-ol (I-5-A) in a two-stage process via (4R,5R)-4,5-dimethyl-2-phenyl-1,3-dioxolane (I-12-A), where the first stage is carried out with pyridinium p-toluenesulphonate in toluene and then a diisobutylaluminium hydride reduction takes place in toluene,

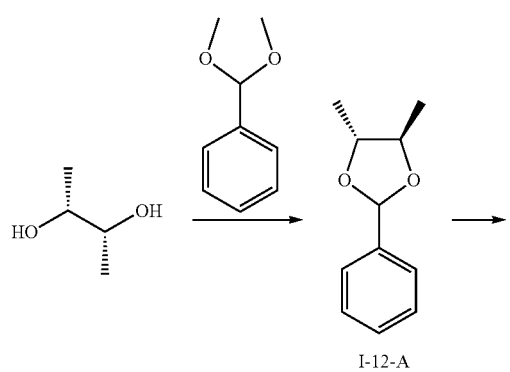

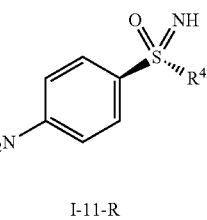

I.g). Coupling of (I-5-A) with 2,4-dichloro-5-trifluoromethylpyrimidine to give 4-{[(2R,3R)-3-(benzyloxy)butan-2-yl]oxy}-2-chloro-5-(trifluoromethyl)pyrimidine (I-7-A) with Li bases in ethereal solvents

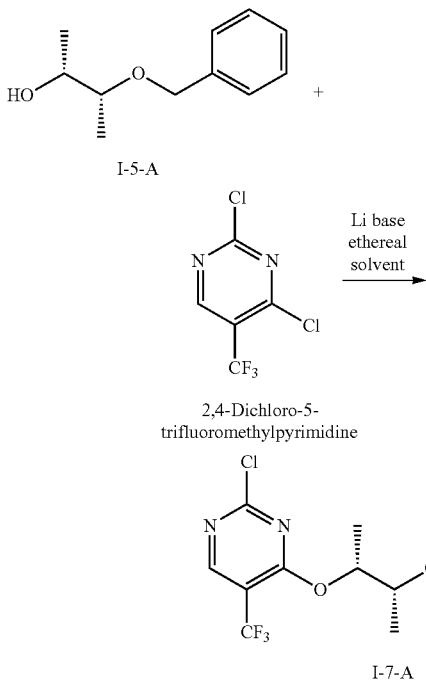

I.h). Preparation of benzenesulphonic acid salts of doubly protected anilino-pyrimidines of the formula (I-8-R-BSA) by benzenesulphonic acid-catalysed coupling of (I-7-A) and (I-4-R)

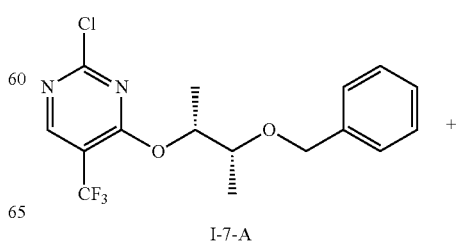

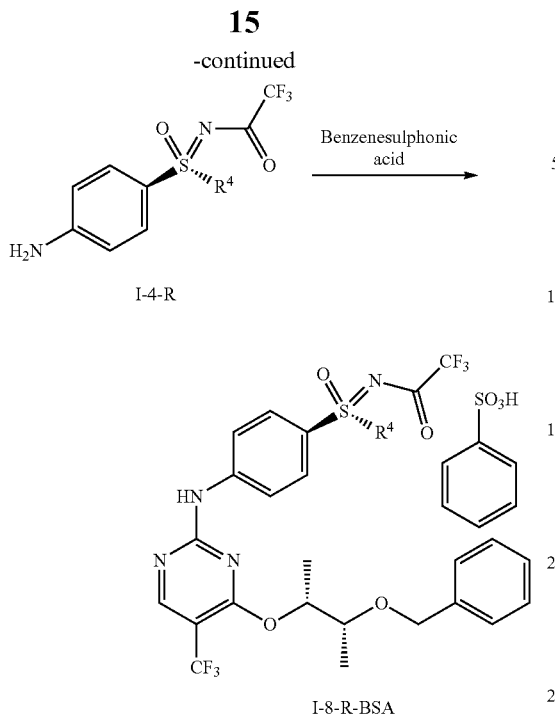

I.i). Cleaving off of the protective groups in benzenesulphonic acid salts of doubly protected anilino-pyrimidines of the formula (I-8-R-BSA) by hydrogenation with palladium on activated carbon and hydrogen in methanol, and also by treatment with potassium carbonate in methanol to give compounds of the formula (I)

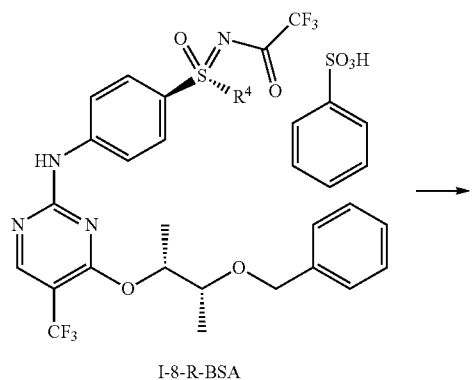

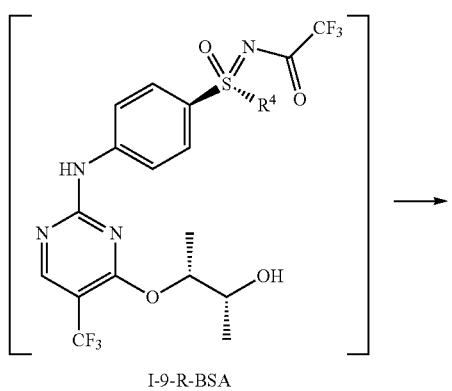

Preparation Steps of the "North Half" of the Compounds According to Formula (I)

I.a) Preparation of Nitrophenyl-Sulphides of the Formula (I-1)

One subject matter of the invention relates to the alkylation step of 4-nitrophenol. The starting material (I-1) was prepared in accordance with WO2010/046035A1 from cyclopropyl sulphide. The latter is not commercially available in large amounts. We therefore switched to an alkylation of commercially available 4-nitrothiophenol with alkylating agents (X—$R^4$) in the presence of an auxiliary base, where X is Br, Cl, I, O—$SO_2$—$CH_3$ or O—$SO_2$-(4-methylphenyl). Suitable bases are sodium carbonate, potassium carbonate or caesium carbonate, preferably potassium carbonate. Suitable solvents are N,N-dimethylformamide, N-methylpyrrolidinone, dimethyl sulphoxide, N,N-dimethylacetamide, preferably N-methylpyrrolidinone.

FIG. 1

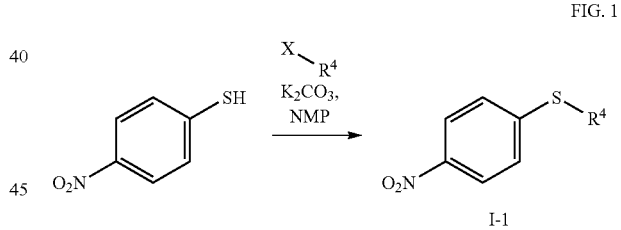

Further subjects of the invention relate to the oxidative amination of nitrophenyl-sulphides of the formula (I-1) to give trifluoroacetate-protected nitrophenyl-sulphilimines of the formula (I-10) (Fig. 2) and the subsequent oxidation to nitrophenyl-sulphoximines of the formula (I-11) (Fig. 3).

I.b) Preparation of the Trifluoroacetate-Protected Nitrophenyl-Sulphilimines of the Formula (I-10)

FIG. 2

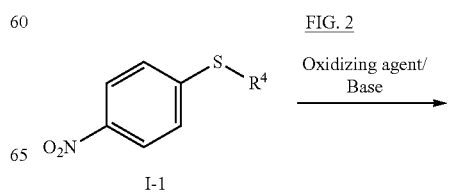

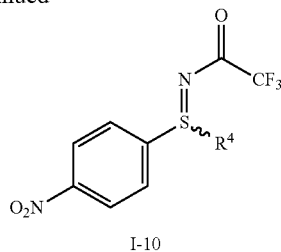

I-10

State of the Art for the Preparation of Sulphilimines

The aim was a direct amination of sulphides to give the trifluoroacetate-protected sulphilimines, that can be readily used for preparative purposes, using simple starting materials such as e.g. 2,2,2-trifluoroacetamide ($CF_3CONH_2$). Carreira et al. (*Org. Lett.* 1999, 1, 149-151) describes the Cu-catalyzed direct amination to give trifluoroacetate-protected sulphilimines with the help of a lithiated TFA-hydroxylamine, but this has to be prepared beforehand in two stages and is not commercially available. This reaction takes place enantioselectively with stoichiometric amounts of a nitride-Mn complex (*Helv. Chim. Acta.* 2002, 3773-3783).

Bolm et al. reports (*Tetrahedron Letters* 2005) that a direct metal-free imination of sulphides is possible. p-Nitrophenyl-sulphonamide (nosylamide, Nos-$NH_2$) and (diacetoxyiodo)benzene (PhI(OAc)$_2$) are proposed, and nosyl-protected sulphilimines are obtained after reflux for 16 h. However, these conditions are not very suitable for a scale-up since the p-nitrophenylsulphonamide protective group can only be removed with difficulty and (diacetoxyiodo)benzene is not commercially available in large amounts.

Suitable oxidizing agents in the reaction according to the invention as in Fig. 2 are, inter alia, N-bromosuccinimide, iodine, sodium hypobromide, 1,3-dibromo-5,5-dimethylhydantoin, N-chlorosuccinimide and trichlorocyanuric acid in the presence of the bases caesium carbonate, potassium tert-butylate, sodium tert-butylate, aqueous sodium hydroxide solution, sodium methanolate, sodium ethanolate, sodium hydride (NaH) in the solvents methanol, dichloromethane, tetrahydrofuran/water, acetonitrile, acetonitrile/water, tetrahydrofuran (THF), propionitrile, methyl tert-butyl ether, 1,4-dioxane, chlorobenzene.

A preferred oxidizing agent is 1,3-dibromo-5,5-dimethyl-hydantoin.

Preferred solvent/base combinations are the combinations acetonitrile/caesium carbonate, 1,4-dioxane/sodium hydride, dichloromethane/potassium tert-butylate, aceonitrile/sodium hydride, tetrahydrofuran/sodium hydride or methyl tert-butyl ether/sodium hydride.

The desired reaction proceeds to completion at just 20° C. within a few hours without adding a catalyst.

Compared to the routes known from the literature, the novel oxidative amination, as shown in Fig. 2, gives rise to the following advantages:
  it is possible to dispense with the expensive and potentially explosion-hazardous (diacetoxyiodo)benzene and also with the addition of metal salts;
  barely any sulphoxide is formed and the reaction proceeds under mild conditions at just 20° C. using commercially available building blocks and reagents;
  the trifluoroacetate group can be hydrolysed very easily (e.g. potassium carbonate in methanol) and is therefore of high preparative value.

It is not only nitrophenyl-sulphides of the formula (I-1) which can be aminated oxidatively according to step I.b). Further trifluoroacetate-protected sulphilimines can also be prepared in this way.

Table 1 shows further sulphilimines accessible using this process step.

TABLE 1

$R^a\text{—S—}R^b$ + [1,3-dibromo-5,5-dimethylhydantoin] $\xrightarrow[\text{THF, 20° C.}]{\text{NaH } CF_3CONH_2}$ trifluoroacetyl-sulphilimine

| Substance | Sulphilimine | Yield |
|---|---|---|
| 1 | 4-($O_2N$)C$_6$H$_4$-S(=NC(O)CF$_3$)-cyclopropyl | 81% |
| 2 | 4-($H_3C$)C$_6$H$_4$-S(=NC(O)CF$_3$)-CH$_3$ | 88% |
| 3 | 4-(MeO)C$_6$H$_4$-S(=NC(O)CF$_3$)-CH$_3$ | 80% |
| 4 | 4-(Cl)C$_6$H$_4$-S(=NC(O)CF$_3$)-CH$_3$ | 75% |
| 5 | cyclohexyl-S(=NC(O)CF$_3$)-CH$_3$ | 74% |

TABLE 1-continued

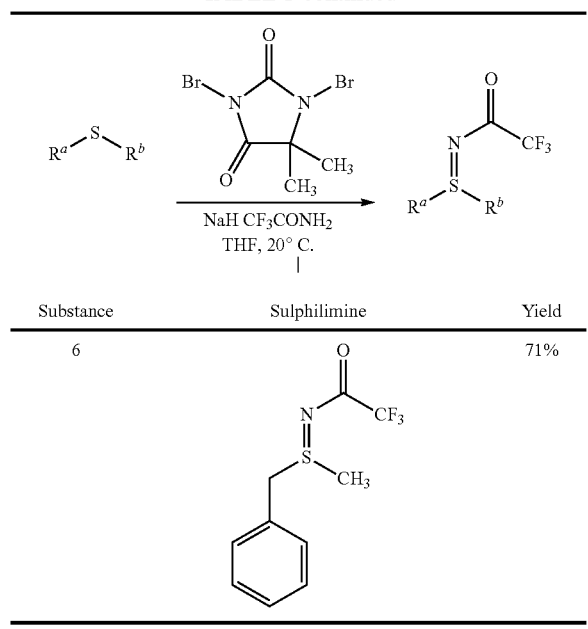

| Substance | Sulphilimine | Yield |
|---|---|---|
| 6 | (structure) | 71% |

I.c) Preparation of Nitrophenyl-Sulphoximines of the Formula (I-11)

The oxidation of the trifluoroacetate-protected nitrophenyl-sulphilimine (I-10) to give the nitrophenyl-sulphoximine (I-11) preferably takes place with potassium peroxomonosulphate (Oxone®) as oxidizing agent.

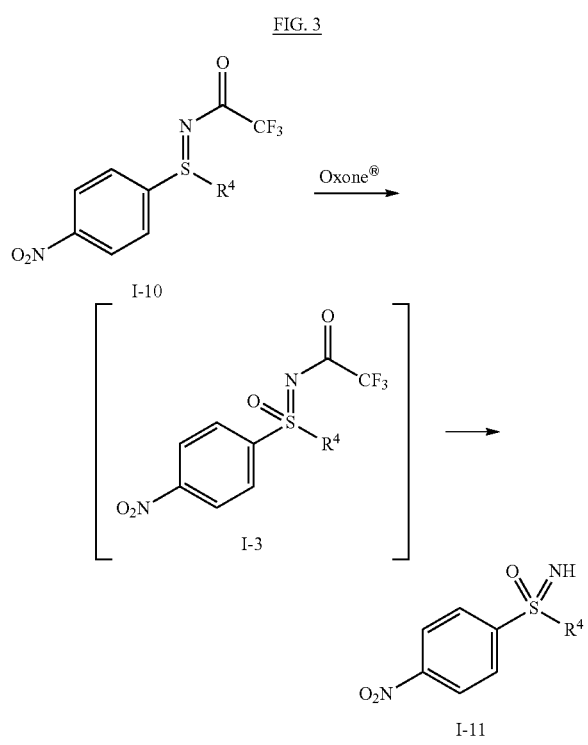

FIG. 3

The desired oxidation proceeds particularly rapidly in the basic pH range. Under these conditions, the trifluoroacetate group is cleaved off at the same time, meaning that the deprotection step which optionally follows can be carried out as a one-pot reaction.

The reaction is particularly preferably carried out in a methanol/water mixture and tetramethylenesulphone (sulpholane) is added as solubility promoter. The potassium peroxomonosulphate (Oxone®) is added in portions and the pH is adjusted to pH 10 after each dosing step.

I.d) Racemate Resolution of Nitrophenyl-Sulphoximines of the Formula (I-11)

A further subject matter of the present invention relates to the racemate resolution of nitrophenyl-sulphoximines of the formula (I-11).

The racemate resolution is based on the following step:

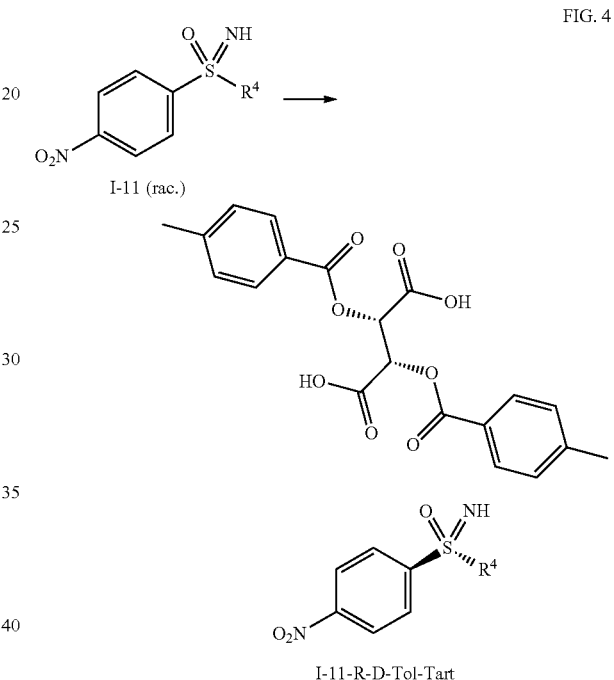

FIG. 4

Surprisingly, it has been found, for example for the nitrophenyl-sulphoximine of the formula (I-11-A) that, using (+)-di-O-p-toluoyl-D-tartaric acid, a ratio of the enantiomers of 95:5 in the crystallizate is obtained. Solvents which can be used are acetonitrile, propionitrile or toluene. Preference is given to acetonitrile or propionitrile.

The crystallization process can be integrated into the preparation process by cleaving off the trifluoroacetate protective group in (I-3) with potassium carbonate in methanol, and reacting the crude nitrophenyl-sulphoximine (I-11) with the (+)-di-O-p-toluoyl-D-tartaric acid to give (I-11-R-D-Tol-Tart.).

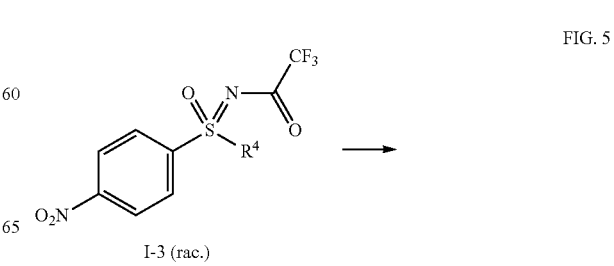

FIG. 5

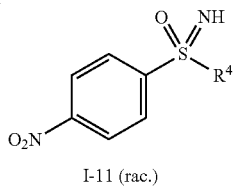

I-11 (rac.)

The toluoyl-D-tartaric acid is removed from the salt by basic extraction and the optically active nitrophenyl-sulphoximine of the formula (I-11-R) can be protected in the one-pot process with trifluoroacetic anhydride in the presence of triethylamine to give (I-3-R).

FIG. 6

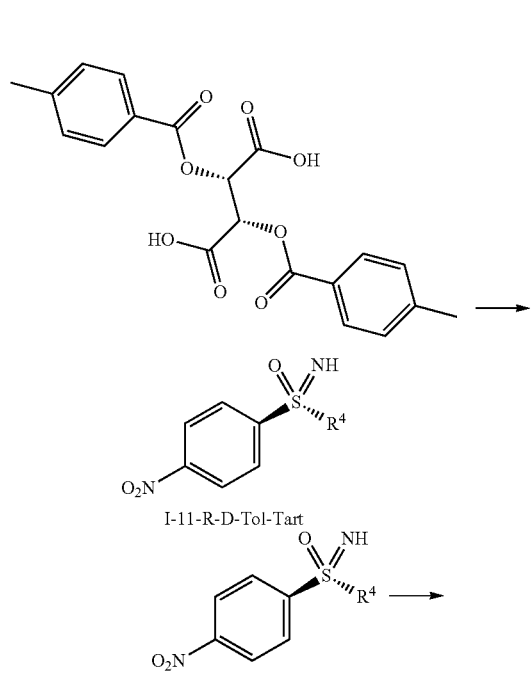

I.e) Hydrogenation of Trifluoroacetate-Protected Nitrophenyl-Sulphoximines of the Formula (I-3-R) to Give Trifluoroacetate-Protected Anilino-Sulphoximines of the Formula (I-4-R)

A further subject matter of the invention relates to the hydrogenation of trifluoroacetate-protected nitrophenyl-sulphoximines (I-3-R) to give trifluoroacetate-protected anilino-sulphoximines of the formula (I-4-R) in the presence of an iron-doped palladium catalyst.

The reduction of the nitro group in the compound (I-3-R) into the corresponding aniline (I-4-R) takes place efficiently by a hydrogenation with immobilized palladium catalysts. Preference is given to iron-doped palladium catalysts on carbon. Solvents which can be used are methanol, ethanol, isopropanol, tetrahydrofuran or acetic acid. Preference is given to methanol.

FIG. 7

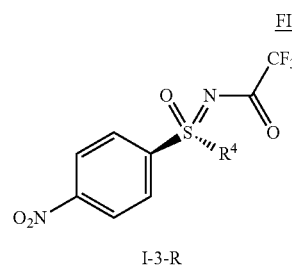

I-3-R

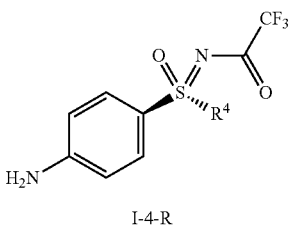

I-4-R

Preparation Steps of the "South Half" of Compounds of the Formula (I)

I.f) Preparation of (R,R)-dimethyldioxolane (I-12-A) and (R,R)-benzylbutanediol (I-5-A)

A further subject matter of the present invention relates to the preparation of (4R,5R)-4,5-dimethyl-2-phenyl-1,3-dioxolane (I-12-A) and (2R,3R)-3-(benzyloxy)butan-2-ol (I-5-A) for the "south half" of compounds of the formula (I).

According to WO2010/046035A1, the commercially available (R,R)-butane-2,3-diol is converted using benzyl chloride in one stage to the monobenzylated (I-5-A). Since, as is expected, the conversion does not proceed selectively to give the mono compound, the reaction mixture has to be purified by means of chromatography and the yields are therefore <50%.

As an alternative, a two-stage process has been presented (*Bioorg. Med. Chem. Lett.* 2006, 16, 186-190).

FIG. 8

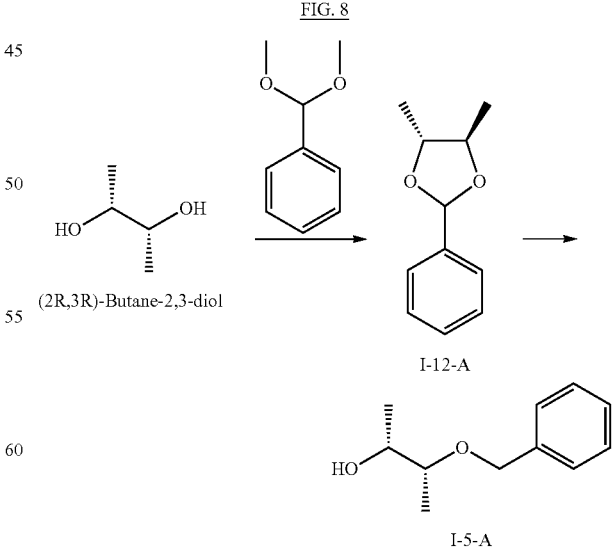

One subject matter of the invention is the clarification of the experimental conditions for a complete conversion, and also a simple isolation and purification which are suitable for an industrial scale. The intermediate (4R,5R)-4,5-dimethyl-2-phenyl-1,3-dioxolane (I-12-A) is obtained in a suitable manner by reacting benzaldehyde dimethyl acetal and an excess of (2R,3R)-butane-2,3-diol in the presence of pyridinium p-toluenesulphonate in toluene as solvent. The reaction was complete at 50° C. within 3 h, during which methanol should be distilled off continuously at reduced pressure.

In the course of the aqueous work-up, the excess diol was removed by extraction. The remaining toluenic phase can be used directly in the subsequent stage.

For the subsequent reduction with diisobutylaluminium hydride (DIBAL), a 1.5 M solution of diisobutylaluminium hydride in toluene was used at 55-60° C. For the work-up, sodium sulphate decahydrate was metered in and the solvent was distilled off after filtration. This gave the compound (I-5-A) in good purities and yields. The product can be used in the subsequent stage without further purification.

I.g) Preparation of 4-{[(2R,3R)-3-(benzyloxy)butan-2-yl]oxy}-2-chloro-5-(trifluoromethyl)pyrimidine (I-7-A)

The nucleophilic monosubstitution of a chlorine atom to give commercially available 2,4-dichloro-5-trifluoromethylpyrimidine preferably proceeds in the 2-position

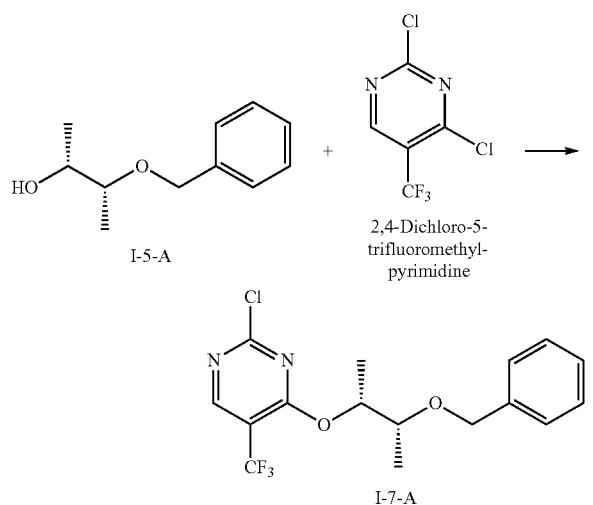

FIG. 9

It has surprisingly been found that the substitution can be steered to the desired 4-position by varying the conditions. It has been shown that Li bases in ethereal solvents at −30° C. produced good conversions and, in the best case, produced a ratio of 4-isomer/2-isomer of 1.2:1. Solvents which can be used are, for example, tetrahydrofuran, 1,2-dimethoxyethane, 1,4-dioxane, methyl tert-butyl ether, diisopropyl ether, n-dibutyl ether, 2-methyltetrahydrofuran or cyclopentyl methyl ether. Preference is given to tetrahydrofuran. Bases which can be used are e.g. lithium hexamethyldisilazide, n-butyllithium, lithium diisopropylamide or lithium-2,2,6,6-tetramethylpiperidine. Preference is given to lithium hexamethyldisilazide. The temperature range is −78° C. to +20° C. The process step according to the invention was derived from this, and operates with lithium hexamethyldisilazide in tetrahydrofuran at −30° C. and produces the desired isomer (I-7-A) following chromatography in yields of up to 46% and purities of >95% area.

Coupling of the North and South Halves and Preparation of the Compounds According to Formula (I)

I.h) Preparation of Anilino-Pyrimidines of the Formula (I-8-R-BSA)

The two building blocks (I-7-A) and (I-4-R) are coupled to give (I-8-R). This reaction is acid-mediated. Suitable acids are, for example, hydrochloric acid, p-toluenesulphonic acid, benzenesulphonic acid, methanesulphonic acid. Preference is given to benzenesulphonic acid.

The free bases (I-8-R) are usually oils, which makes purification and also storage more complicated. Surprisingly, it has been found that when using benzenesulphonic acid, the resulting benzenesulphonic acid salts (I-8-R-BSA) crystallize out of the reaction mixture. The salts (I-8-R-BSA) can be purified by crystallization and are storage-stable.

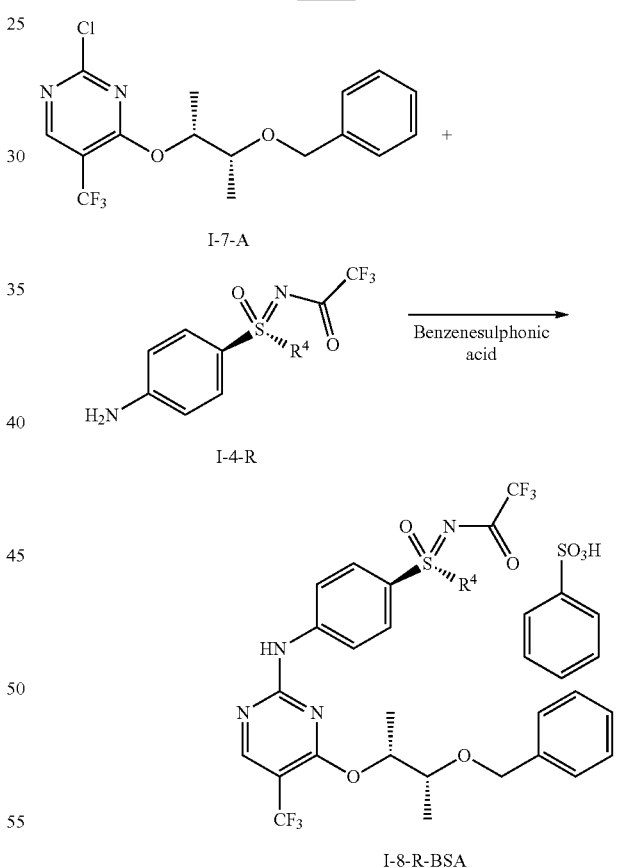

FIG. 10

Alternatively, toluenesulphonic acid or methanesulphonic acid can be used.

I.i) Preparation of the Compounds of the Formula (I)

In the last two steps, the protective groups are cleaved off (Fig. 11).

FIG. 11

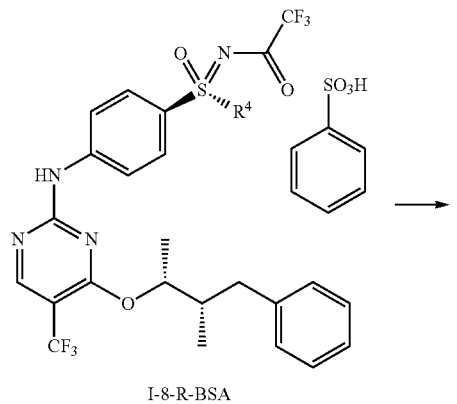

I-8-R-BSA

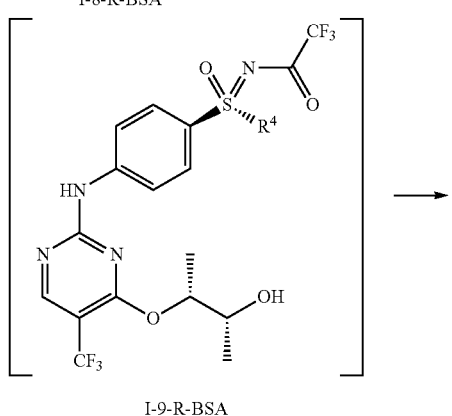

I-9-R-BSA

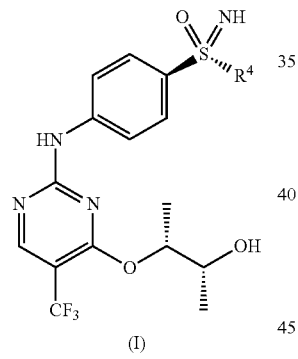

(I)

The hydrogenation at atmospheric pressure takes place with palladium/carbon and hydrogen in methanol within a few hours to give the intermediate of the formula (I-9-R-BSA).

The intermediate of the formula (I-9-R-BSA) can be further reacted directly to give the end stage. The cleaving off of the group can be completed with potassium carbonate and the crystallization of the end stage takes place from ethyl acetate/n-heptane.

II. Intermediates

Further subjects of the present invention are the following intermediates

II. a) Trifluoroacetate-protected nitrophenyl-sulphilimines of the formula (I-10), in particular (I-10-A)

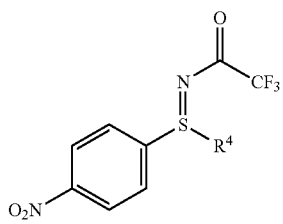
I-10

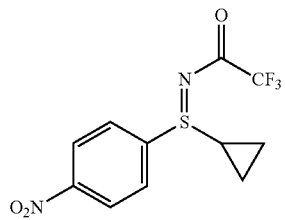 [SMILES: O=C(/N=S(/c1ccc([N+](=O)[O-])cc1)C1CC1)C(F)(F)F]
I-10-A

II. b) Nitrophenyl-sulphoximines of the formula (I-11-R), in particular (I-11-A) and (I-11-A-R)

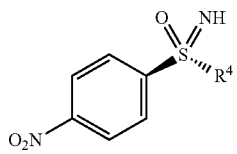
I-11-R

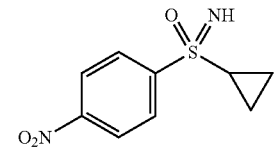
I-11-A

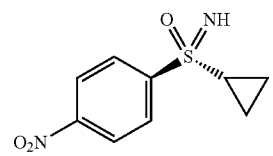
I-11-A-R

II. c) (R)-enantiomers of trifluoroacetate-protected nitrophenyl-sulphoximines of the formula (I-3-R), in particular (I-3-A-R)

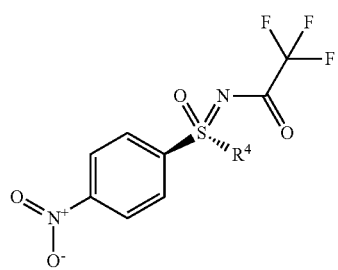
(I-3-R)

-continued (I-3-A-R)

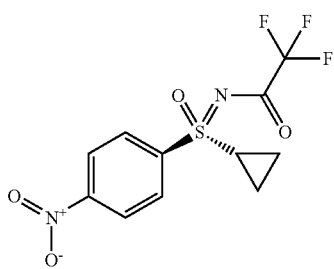

II. d) Salts (I-11-R-D-Tol-Tart.) of the nitrophenyl-sulphoximines of the formula (I-11-R) with (+)-di-O-p-toluoyl-D-tartaric acid, in particular (I-11-A-R-D-Tol-Tart.)

I-11-R-D-Tol-Tart

I-11-A-R-D-Tol-Tart

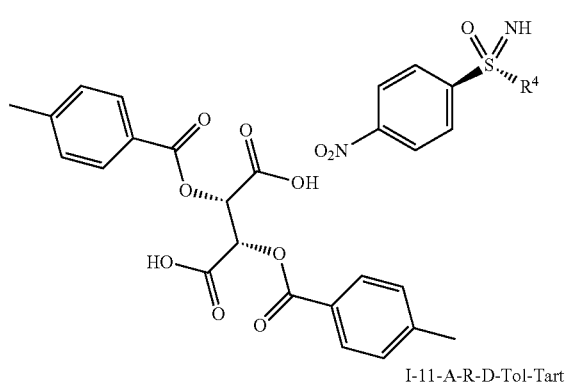

I.e) Anilinopyrimidines of the formula (I-8-R-BSA), in particular (I-8-A-R-BSA)

I-8-R-BSA

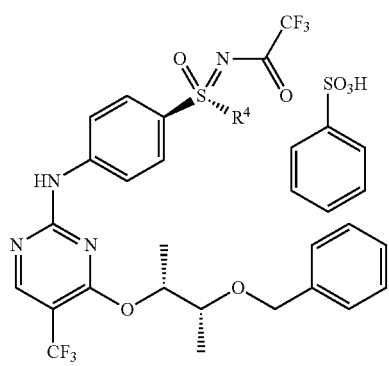

-continued

I-8-A-R-BSA

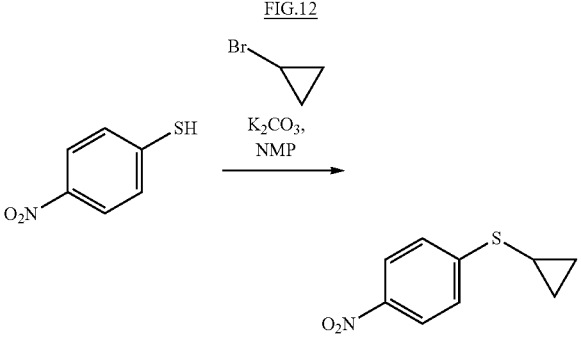

where $R^4$ is in each case a $C_1$-$C_6$-alkyl group or a $C_3$-$C_7$-cycloalkyl ring.

I-A. Preparation of the Compound A

Preparation of the "North Half" of Compound A

I-A.a) Preparation of cyclopropyl-nitrophenyl-sulphide (I-1-A)

In the first step of the reaction sequence, 4-nitrothiophenol is alkylated with bromocyclopropane in the presence of potassium carbonate. The desired reaction proceeds in N-methylpyrrolidinone (NMP) within 8-10 h at a preferred temperature of 135° C.

FIG. 12

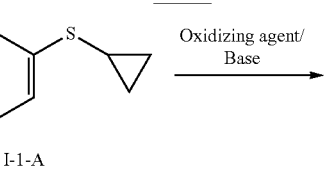

The isolation of (I-1-A) was carried out by metering the reaction mixture on to ice-water, and the crude crystallizate was isolated with a good purity of typically 89-93 area % with a yield of 82-87%.

I-A.b) Preparation of the trifluoroacetate-protected cyclopropyl-nitrophenyl-sulphilimine (I-10-A)

FIG. 13

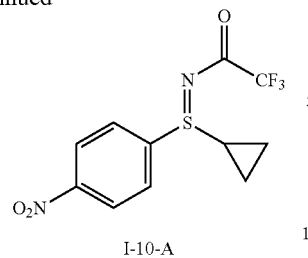

I-10-A

In the second step, an oxidative amination to give the trifluoroacetate-protected cyclopropyl-nitrophenyl-sulphilimine (I-10-A) takes place.

In a broad screening, the conversion of the cyclopropyl-nitrophenyl-sulphide (I-1-A) into the trifluoroacetate-protected cyclopropyl-nitrophenyl-sulphilimine (I-10-A) was investigated. Suitable oxidizing agents in the reaction according to the invention as in Fig. 13 are N-bromosuccinimide, 1,3-dibromo-5,5-dimethylhydantoin in the presence of the bases potassium tert-butylate, sodium hydride in the solvents dichloromethane, tetrahydrofuran or acetonitrile. The desired reaction proceeds in a temperature window from 0-50° C., with 20° C. being preferred.

The oxidizing agents tested were 1,3-dibromo-5,5-dimethylhydantoin, N-chlorosuccinimide and trichlorocyanuric acid in the presence of the bases potassium tert-butylate, sodium tert-butylate, aqueous sodium hydroxide solution, sodium hydroxide, sodium methanolate, sodium hydride in the solvents methanol, dichloromethane, tetrahydrofuran/water, acetonitrile, acetonitrile/water, tetrahydrofuran, propionitrile, methyl tert-butyl ether, dioxane, chlorobenzene.

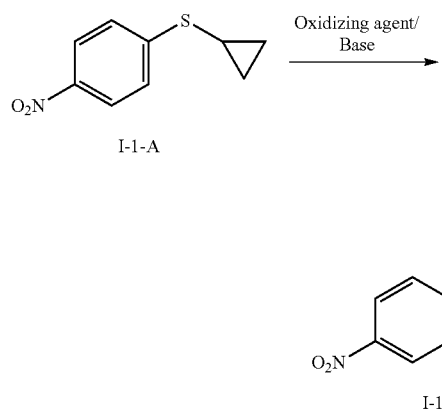

FIG. 14

In the course of the reaction, the sodium hydride in tetrahydrofuran was introduced as initial charge and cyclopropyl-nitrophenyl-sulphide (I-1-A) was added dropwise with trifluoroacetamide. With cooling, a solution of 1,3-dibromo-5,5-dimethylhydantoin in tetrahydrofuran was metered in and the mixture was stirred at room temperature. Work-up is by reductive (sodium sulphite) means, and crystallization from diisopropyl ether/n-heptane was performed. This gave the product (I-10-A) in good yields and purities.

I-A.c) Preparation of 1-(cyclopropylsulphonimidoyl)-4-nitrobenzene (I-11-A)

The oxidation of the trifluoroacetate-protected nitrophenyl-sulphilimine ((I-10-A)) to give 1-(cyclopropylsulphonimidoyl)-4-nitrobenzene (I-11-A) preferably takes place with potassium peroxomonosulphate (Oxone®) as oxidizing agent.

FIG. 15

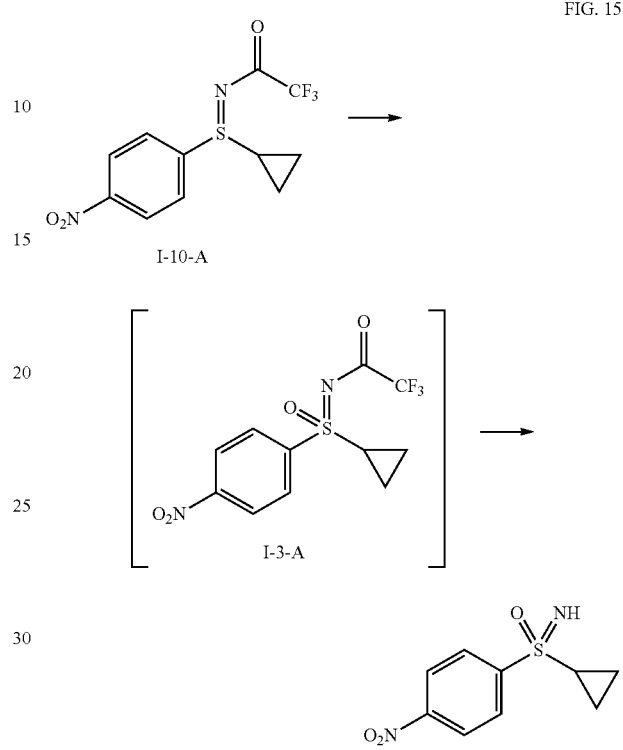

The reaction was carried out in a methanol/water mixture and tetramethylenesulphone (sulpholane) was added as solubility promoter. The potassium peroxomonosulphate (Oxone®) is added in portions and the pH is adjusted to pH 10 after each dosing step.

After 5 h, 99% conversion is already observed to the desired racemic 1-(cyclopropylsulphonimidoyl)-4-nitrobenzene (I-11-A). Work-up is by aqueous (sodium sulphite) means and the product is crystallized from the organic phase (methylene chloride) after drying over magnesium sulphate from n-heptane.

I-A.d) Racemate resolution of 1-(cyclopropylsulphonimidoyl)-4-nitrobenzene (I-11-A)

The racemate resolution is based on the following step:

FIG. 16

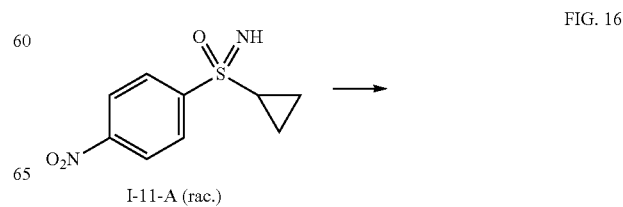

I-11-A (rac.)

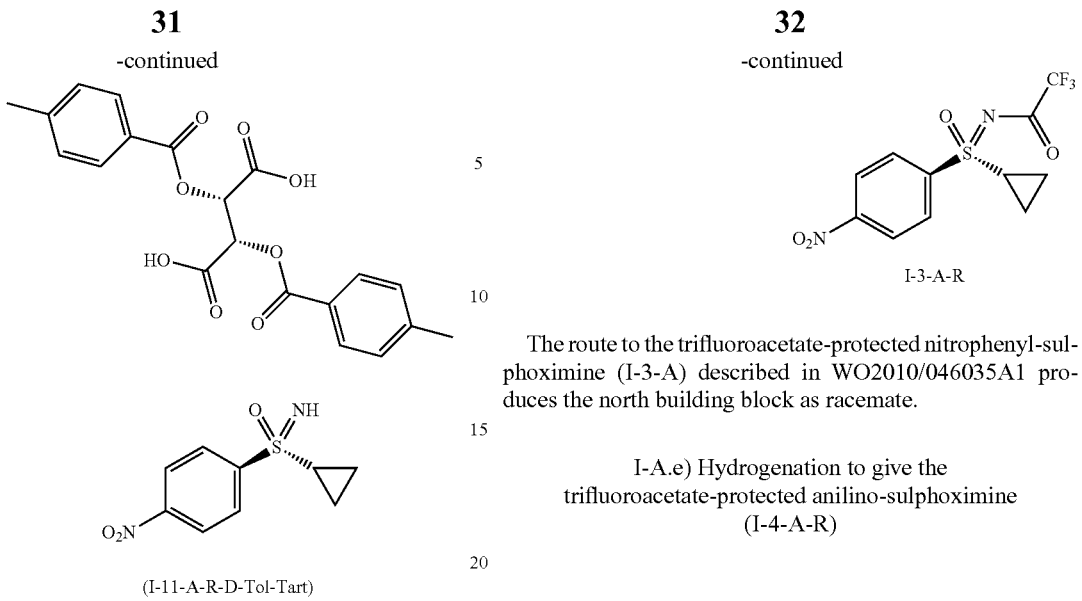

(I-11-A-R-D-Tol-Tart)

Surprisingly, it has been found that with (+)-di-O-p-toluoyl-D-tartaric acid in acetonitrile, a ratio of the enantiomers of at least 95:5 in the crystallizate is obtained. The yields were 40-45%. Alternatively to acetonitrile, it is also possible to use propionitrile. The optical purity can be further improved by recrystallization from acetonitrile or propionitrile.

The crystallization process can be integrated into the preparation process by cleaving off the trifluoroacetate protective group in (I-3-A) with potassium carbonate in methanol and reacting crude nitrophenyl-sulphoximine (I-11-A) with (+)-di-O-p-toluoyl-D-tartaric acid in acetonitrile to give (I-11-A-D-Tart.).

The optically active nitrophenyl-sulphoximine is released by basic extraction and then protected in the one-pot process with trifluoroacetic anhydride in the presence of triethylamine to give (I-3-A-R).

FIG. 17

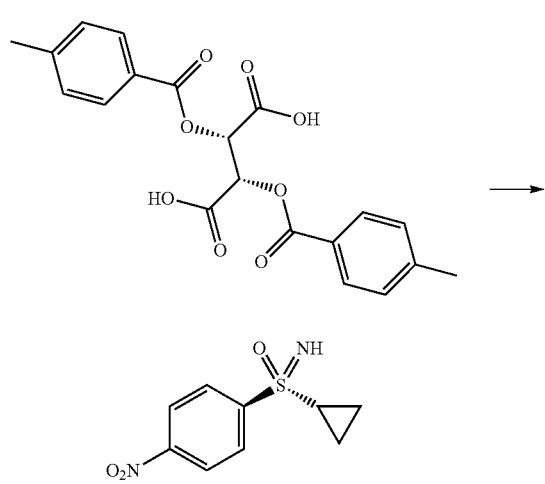

I-11-A-R-D-Tol-Tart

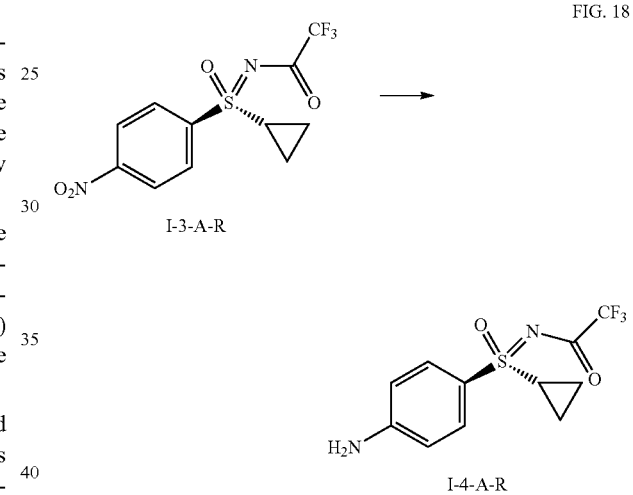

I-3-A-R

The route to the trifluoroacetate-protected nitrophenyl-sulphoximine (I-3-A) described in WO2010/046035A1 produces the north building block as racemate.

I-A.e) Hydrogenation to give the trifluoroacetate-protected anilino-sulphoximine (I-4-A-R)

FIG. 18

Conversion of the nitro group in the compound (I-3-A-R) to the corresponding aniline (I-4-A-R) takes place via a hydrogenation with immobilized palladium catalysts. A particularly clean product is obtained by using iron-doped palladium catalysts on carbon. Methanol is preferred as solvent. The trifluoroacetate-protected anilino-sulphoximine (I-4-A-R) can be isolated after crystallization with a yield of at least 88%.

Preparation of the "South Half" of Compound A

The construction of the south half of compound A takes place according to the invention as in I.g) and II).

Coupling of North and South Halves

I-A.h) Preparation of N-[(4-{[4-{[(2R,3R)-3-(benzyloxy)butan-2-yl]oxy}-5-(trifluoromethyl)pyrimidin-2-yl]amino}phenyl)(cyclopropyl)oxido-lambda$^6$-sulphanylidene]-2,2,2-trifluoroacetamide benzenesulphonic acid salt (I-8-A-R-BSA)

In the first step, the two building blocks (I-7-A) and (I-4-A-R) are coupled to give (I-8-A-R). This reaction is acid-mediated. The free base (I-8-A-R) is an oil. Surprisingly, it has been found that when using 1,4-dioxane as solvent, the resulting benzenesulphonic acid salt (I-8-A-R-BSA) crystallizes from the reaction mixture.

FIG. 19

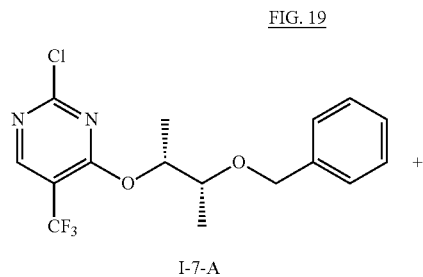

The crystallization can be completed with n-heptane, and the desired N-[(4-{[4-{[(2R,3R)-3-(benzyloxy)butan-2-yl]oxy}-5-(trifluoromethyl)pyrimidin-2-yl]amino}phenyl)(cyclopropyl)oxido-lambda$^6$-sulphanylidene]-2,2,2-trifluoroacetamidee benzenesulphonic acid salt is obtained in good yields. The salt (1-8.A-R-BSA) is crystalline and storable and it is isolated with a typical purity of ca. 90 area %.

I-A.i) Preparation of the Compound A

In the last two steps, the protective groups are cleaved off (Fig. 20).

FIG. 20

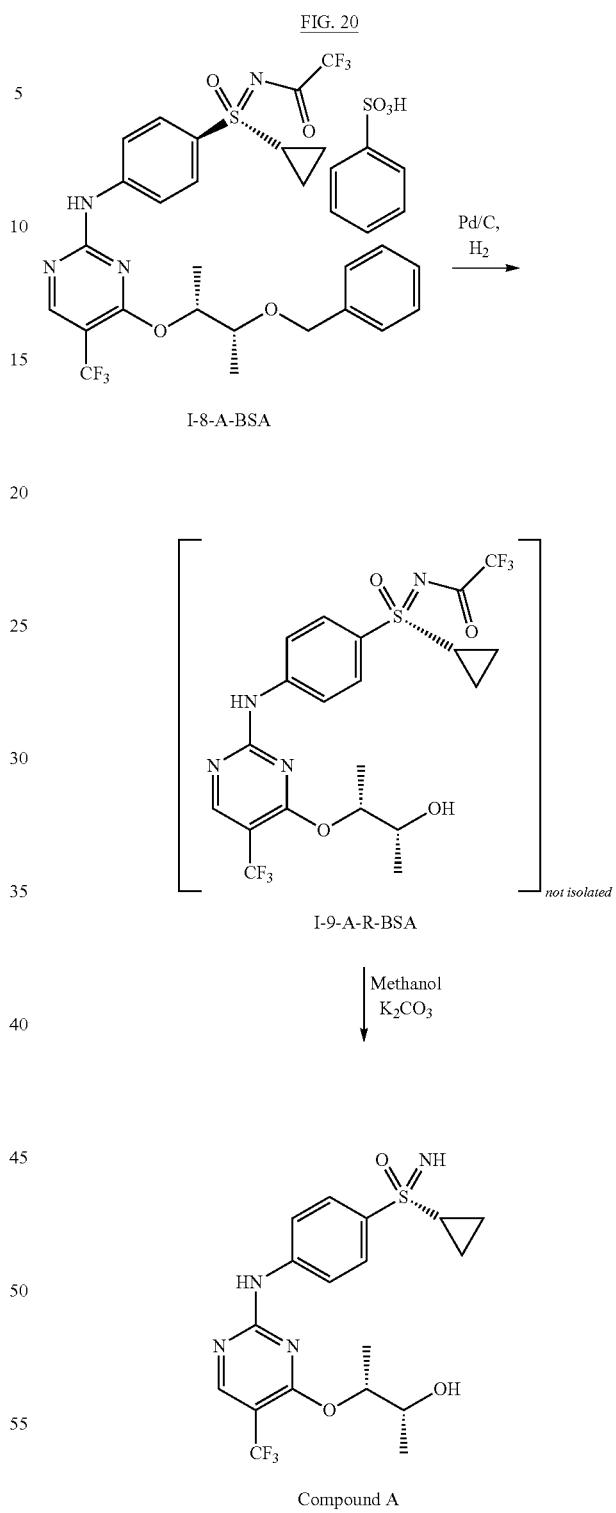

The intermediate I-9-A-R-BSA was not isolated, but further reacted directly to give the end stage. The cleaving off of the trifluoroacetate group was completed with potassium carbonate in methanol and the crystallization of the end stage was performed from a mixture of ethyl acetate/heptane.

7. Concordance

TABLE 2

| Name | Article name | Structure | IUPAC name | MW |
|---|---|---|---|---|
| I-1 | nitrophenyl-sulphide | 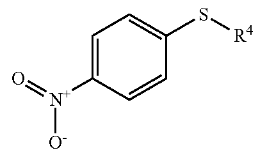 | | |
| I-1-A | cyclopropyl-nitrophenyl-sulphide | 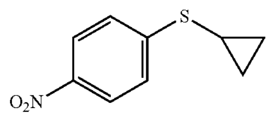 | 1-(cyclopropylsulphanyl)-4-nitrobenzene | 195.24 |
| I-2 | nitrophenyl-sulphoxide | 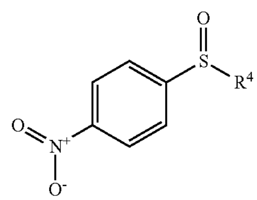 | | |
| I-3 | trifluoroacetate-protected nitrophenyl-sulphoximine | 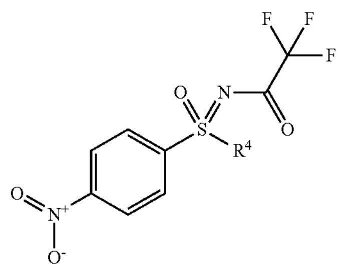 | | |
| I-3-R | (R) enantiomer of the trifluoroacetate-protected nitrophenyl-sulphoximine | 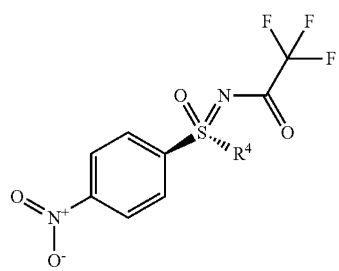 | | |
| I-3-A-R | (R) enantiomer of the trifluoroacetate-protected cyclopropyl-nitrophenyl-sulphoximine | 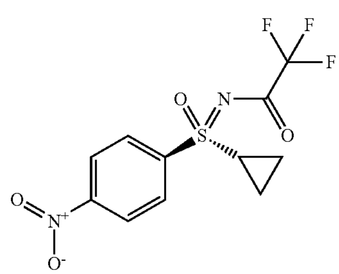 | N-[(R)-cyclopropyl(4-nitrophenyl)oxido-lambda$^6$-sulphanylidene]-2,2,2-trifluoroacetamide | 322.26 |
| I-4 | trifluoroacetate-protected anilino-sulphoximine | 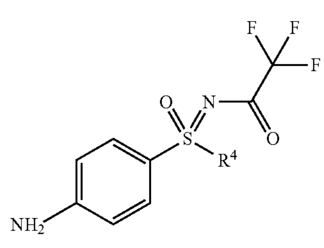 | | |

TABLE 2-continued

| Name | Article name | Structure | IUPAC name | MW |
|---|---|---|---|---|
| I-4-R | (R) enantiomer of the trifluoroacetate-protected anilino-sulphoximine | 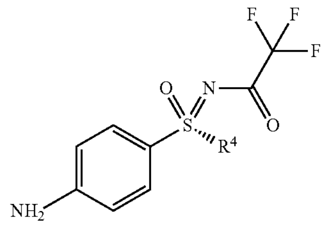 | | |
| I-4-A-R | (R) enantiomer of the trifluoroacetate-protected cyclopropyl-anilino-sulphoximine | 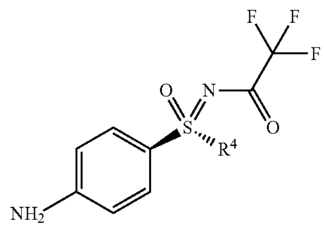 | N-[(R)-(4-aminophenyl)(cyclopropyl)oxido-lambda$^6$-sulphanylidene]-2,2,2-trifluoroacetamide | 292.28 |
| I-5-A | | 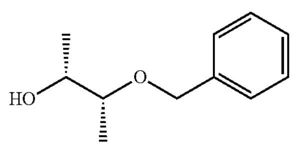 | (2R,3R)-3-(benzyloxy)butan-2-ol | 180.25 |
| I-6 | protected hydroxyalkoxy-pyrimidine | 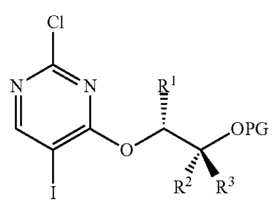 | | |
| I-7 | protected CF$_3$ intermediate | 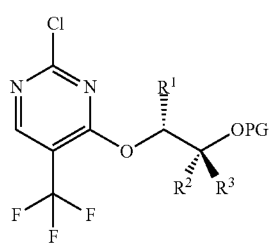 | | |
| I-7-A | benzyl-protected CF$_3$ intermediate | 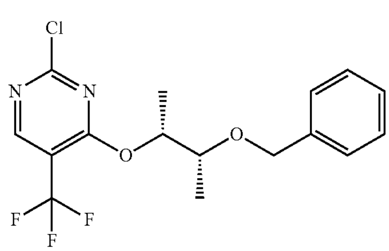 [SMILES: C[C@@H](OCc1ccccc1)[C@@H](C)Oc1nc(Cl)ncc1C(F)(F)F] | 4-{[(2R,3R)-3-(benzyloxy)butan-2-yl]oxy}-2-chloro-5-(trifluoromethyl)pyrimidine | 360.77 |

| Name | Article name | Structure | IUPAC name | MW |
|---|---|---|---|---|
| I-8 | doubly protected anilinopyrimidines | 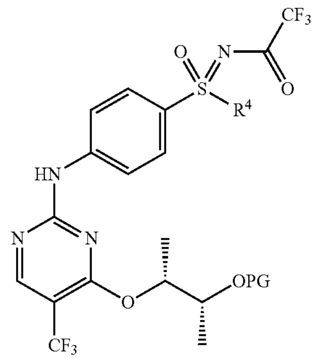 | | |
| I-8-R-BSA | benzenesulphonic acid salt of doubly protected anilinopyrimidines | 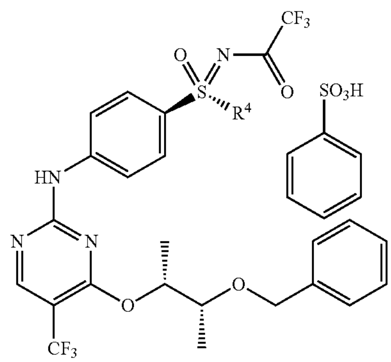 | | |
| I-8-A-R-BSA | benzenesulphonic acid salt of doubly protected cyclopropylanilino-pyrimidines | 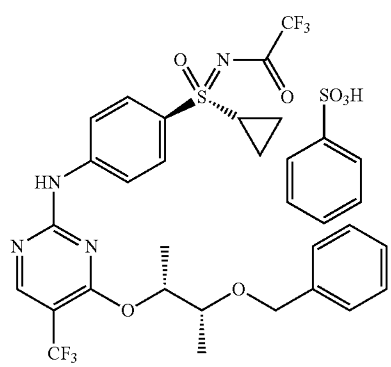 | N-[(4-{[4-{[(2R,3R)-3-(benzyloxy)butan-2-yl]oxy}-5-(trifluoromethyl)pyrimidin-2-yl]amino}phenyl)(cyclopropyl) oxide o-lambda⁶-sulphanylidene]-2,2,2-trifluoroacetamide benzenesulphonic acid salt (1:1) | 774.76 |
| I-9 | singly protected anilinopyrimidines | 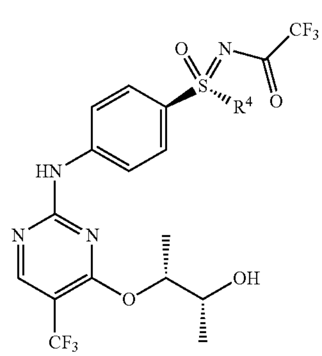 | | |

TABLE 2-continued

| Name | Article name | Structure | IUPAC name | MW |
|---|---|---|---|---|
| I-9-R-BSA | benzenesulphonic acid salt of singly protected anilinopyrimidines | 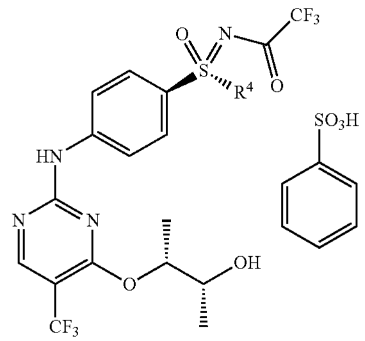 | | |
| I-9-A-R-BSA | benzenesulphonic acid salt of singly protected cyclopropylanilino-pyrimidines | 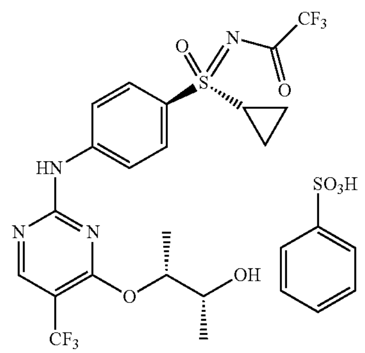 | N-[cyclopropyl(4-{[4-{[(2R,3R)-3-hydroxybutan-2-yl]oxy}-5-(trifluoromethyl)pyrimidin-2-yl]amino}phenyl)oxido-lambda⁶-sulphanylidene]-2,2,2-trifluoroacetamide benzenesulphonic acid salt (1:1) | 684.64 |
| I-10 | trifluoroacetate-protected nitrophenyl-sulphilimine | 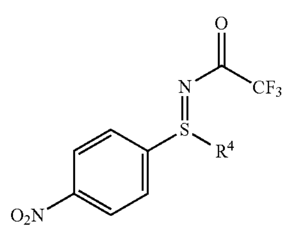 | | |
| I-10-A | trifluoroacetate-protected cyclopropyl-nitrophenyl-sulphilimine | 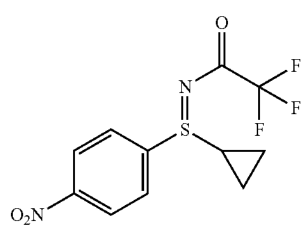 [SMILES: O=C(/N=S(/c1ccc([N+](=O)[O-])cc1)C1CC1)C(F)(F)F] | N-[cyclopropyl(4-nitrophenyl)-lambda⁴-sulphanylidene]-2,2,2-trifluoroacetamide | 306.27 |
| I-11 | nitrophenyl-sulphoximine | 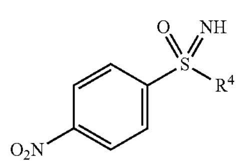 | | |
| I-11-R | R enantiomer of the nitrophenyl-sulphoximine | 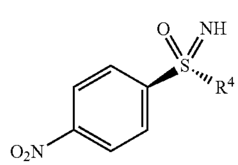 | | |

TABLE 2-continued

| Name | Article name | Structure | IUPAC name | MW |
|------|--------------|-----------|------------|-----|
| I-11-A | cyclopropyl-nitrophenyl-sulphoximine | 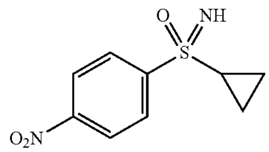 [SMILES: N=S(=O)(c1ccc([N+](=O)[O-])cc1)C1CC1] | 1-(cyclopropylsulphonimidoyl)-4-nitrobenzene | 226.26 |
| I-11-A-R | R enantiomer of the cyclopropyl-nitrophenyl-sulphoximine | 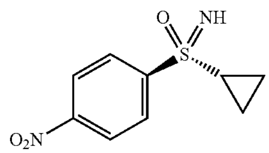 | 1-(R-cyclopropylsulphonimidoyl)-4-nitrobenzene | 226.26 |
| I-11-R-D-Tol-Tart. | toluoyl-D-tartaric acid salt of the R-enantiomer of nitrophenyl-sulphoximine | 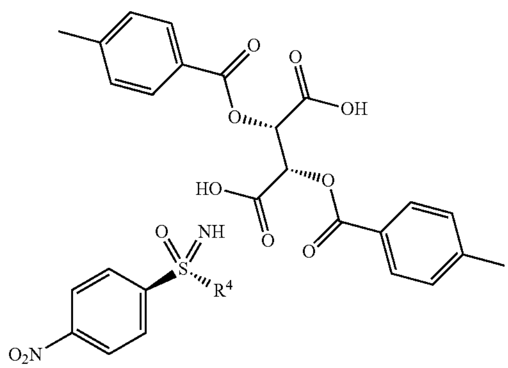 | 1-(R)-(cyclopropylsulphonimidoyl)-4-nitrobenzene | |
| I-11-A-R-D-Tol-Tart. | toluoyl-D-tartaric acid salt of the R-enantiomer of cyclopropyl-nitrophenyl-sulphoximine | 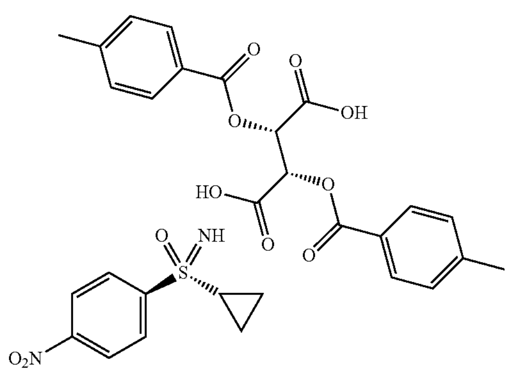 | (2S,3S)-2,3-bis[(4-methylbenzoyl)oxy]succinic acid-1-(R-cyclopropylsulphonimidoyl)-4-nitrobenzene (1:1) | 612.62 |
| I-12-A | | 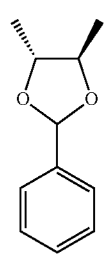 | (4R,5R)-4,5-dimethyl-2-phenyl-1,3-dioxolane | 178.23 |

TABLE 2-continued

| Name | Article name | Structure | IUPAC name | MW |
|---|---|---|---|---|
| Compound A | compound A | 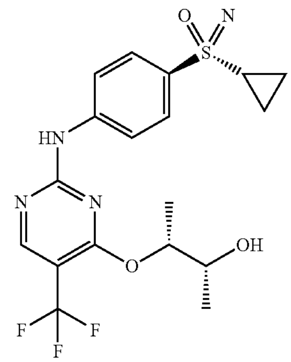 | (2R,3R)-3-{[2-{[4-(R-cyclopropylsulphonimidoyl)phenyl]amino}-5-(trifluoromethyl)pyrimidin-4-yl]oxy}butan-2-ol | 430.45 |
| Compound of the formula (I) | | 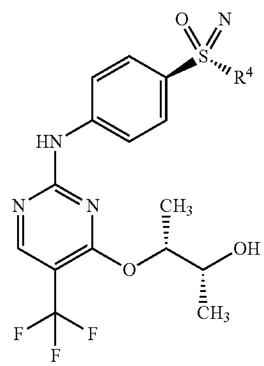 | | |

EXAMPLE

Preparation of 1-(cyclopropylsulphanyl)-4-nitrobenzene (I-1-A)

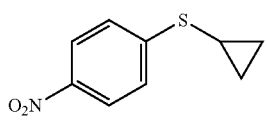

I-1-A

A solution of 80 g (0.51 mol) of 4-nitrothiophenol (80%) in 400 ml of N-methylpyrrolidinone (NMP) was added over the course of 30 min to a suspension of 92.6 g (0.67 mol) of potassium carbonate in 400 ml of NMP. The temperature increased during this to 30° C.

93.6 g (0.77 mol) of cyclopropyl bromide were added to the reaction mixture, which was stirred for 8 h at 135-140° C. The mixture was cooled to 20° C. and admixed with 4.0 g of activated carbon. The following were then carried out: heating to 65° C., stirring for one hour, filtering and after-washing with 80 ml of NMP. The mixture was cooled to 20° C. and metered over the course of 1 h on to 3 l of water. Filtration was carried out and the filter cake was washed three times with in each case 400 ml of water. The mixture was then stirred with 800 ml of a 1 M aq. hydrochloric acid and filtered again, and the filter cake was washed three times with in each case 400 ml of water. Finally, it was dried in vacuo at 40° C., giving 86.6 g (86%) of the title compound (I-1-A) with a purity of 91.2 area %.

The crude material can be further purified. For this 90 g of the crude material are dissolved in 700 ml of n-heptane, heated to 65° C., ca. 400 ml of n-heptane is distilled off and seed crystals are added while cooling to 20° C. The mixture is stirred for one hour at 0-5° C. and filtered, and the residue is washed with 100 ml of cold n-heptane. After drying, 81 g of the title compound (I-1-A) with a purity of 100 area % are obtained.

NMR and MS analysis: Luecking, Ulrich; Krueger, Martin; Jautelat, Rolf; Siemeister, Gerhard. Preparation of pyrimidinylaminoarylsulphoximines as cyclin dependent kinase (CDK) and/or vascular endothelial growth factor (VEGF) inhibitors: WO 2005037800, page 105.

HPLC method A: Column Zorbax SB-Aq 150×3 mm, 3.5 µM; gradient: 0-20 min from 95% aq. phosphate buffer pH 2.4/5% acetonitrile to 20% aq. phosphate buffer pH 2.4/80% acetonitrile, flow: 0.5 ml/min, detection at 210 nm, T=45° C.;

Retention time of (I-1-A) with method A: 16.7 min

Preparation of N-[cyclopropyl(4-nitrophenyl)-lambda$^4$-sulphanylidene]-2,2,2-trifluoroacetamide (I-10-A)

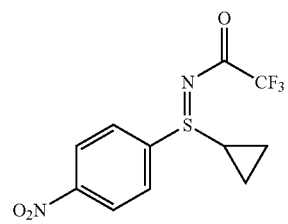

I-10-A

A solution of 11.5 g (58.9 mmol) of 1-(cyclopropylsulphanyl)-4-nitrobenzene (I-1-A) and 10.0 g (88.4 mmol) of 2,2,2-trifluoroacetamide in 46 ml of tetrahydrofuran (THF) was metered at 0-5° C. over the course of 30 min into a suspension of 2.1 g (53 mmol) of sodium hydride (60% in mineral oil) in 50 ml of tetrahydrofuran.

A solution of 25.3 g (88.4 mmol) of 1,3-dibromo-5,5-dimethylhydantoin in 86 ml of tetrahydrofuran was added to the reaction mixture at 20-25° C. over the course of 15 min and the mixture was after-stirred for 14 h.

For the work-up, 70 ml of a 25% strength sodium sulphite solution and 140 ml of toluene were added. The organic phase was washed three times with in each case 140 ml of water, concentrated in vacuo to ca. 80 g, admixed with 40 ml of n-heptane and after-stirred for 1.5 h at 20° C. The following were carried out: filtration, washing twice with in each case 25 ml of n-heptane and drying in vacuo at 40° C. This gave 14.5 g of the title compound (I-10-A) with 100 area % purity. This corresponded to a yield of 80.8%.

Larger Scale:

A solution of 80.0 g (409.8 mmol) of 1-(cyclopropylsulphanyl)-4-nitrobenzene (I-1-A) and 69.5 g (614.6 mmol) of 2,2,2-trifluoroacetamide in 320 ml of THF were metered in to a suspension of 14.8 g (368.8 mmol) of sodium hydride (60% in mineral oil) in 360 ml of THF at 0-5° C. over the course of 45 min.

A solution of 175.7 g (614.6 mmol) of 1,3-dibromo-5,5-dimethylhydantoin in 550 ml of THF was then added at 0-5° C. over the course of 45 min. The mixture was thawed to 20° C. and left to stand for 14 h. For the work-up, 560 ml of a 10% citric acid solution and 1.1 l of toluene were added. The organic phase was washed with 560 ml of a 25% sodium sulphite solution and three times with in each case 650 ml of water. The organic phase was concentrated in vacuo to ca. 750 g and admixed with 525 g of n-heptane. The following were carried out: after-stirring for 1 h at room temperature, filtration with suction and washing with 50 ml of a 1:1 mixture of toluene/heptane. Drying in vacuo gave 90.7 g (72% yield) of the title compound (I-10-A) with 99.1 area % purity.

HPLC method A: retention time for (I-10-A): 14.8 min.
MS (CI): [M+H]$^+$=307, [M+NH$_4$]$^+$=324
$^1$H NMR (400 MHz, DMSO-d$_6$) δ ppm 1.09-1.19 (m, 1H) 1.21-1.38 (m, 3H) 3.03-3.15 (m, 1H) 8.13-8.23 (m, 2H) 8.42-8.54 (m, 2H).

Preparation of 1-(S-cyclopropylsulphonimidoyl)-4-nitrobenzene (I-11-A)

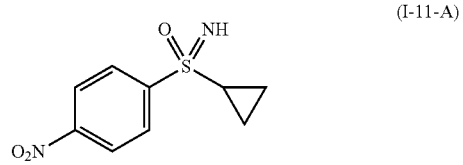 [SMILES: N=S(=O)(c1ccc([N+](=O)[O-])cc1)C1CC1]

(I-11-A)

To a solution of 100.0 g (326.5 mmol) of (I-10-A) in 850 ml of methanol, 130 ml of tetramethylensulphone (sulpholane) and 590 ml of water were added 341.2 g (555.1 mmol) of potassium peroxomonosulphate (Oxone®) spread over eight portions at 25° C. After each addition, the pH was adjusted to pH 10 using a 47% aqueous potassium carbonate solution. In total, ca. 350 ml of potassium carbonate solution were used. The conversion was complete after one hour at 25° C. 960 ml of dichloromethane were added and the mixture was stirred for 1 h at 20° C. It was filtered with suction and the residue was washed twice with in each case 400 ml of dichloromethane. The combined organic phase was washed with 400 ml of a 10% aqueous sodium sulphite solution and four times with in each case 1 l of water. After separating the phases, drying was carried out over magnesium sulphate and concentration to ca. 450 g. 100 ml of n-heptane were added, and the mixture was concentrated in vacuo to ca. 400 ml and after-stirred for one hour at 0-5° C. It was filtered with suction and the residue was washed twice with in each case 100 ml of cold n-heptane. Finally, the mixture was dried in vacuo at 40° C., giving 68.5 g (92.8%) of the title compound (I-11-A) with a purity of 100 area %.

HPLC method A: retention time for (I-11-A): 9.5 min
MS (CI): [M+H]$^+$=227
$^1$H NMR (400 MHz, DMSO-d$_6$) δ ppm 0.86-1.06 (m, 3H) 1.15 (dt, J=9.96, 4.19 Hz, 1H) 2.69-2.88 (m, 1H) 4.65 (s, broad, 1H) 8.15 (d, J=8.80 Hz, 2H) 8.41 (d, J=8.56 Hz, 2H).

Preparation of (2S,3S)-2,3-bis[(4-methylbenzoyl)oxy]butanedioic acid-N—[(R)-cyclopropyl(4-nitrophenyl)oxido-lambda$^6$-sulphanylidene]-2,2,2-trifluoroacetamide (1:1) (I-11-A-R-D-Tol-Tart.)

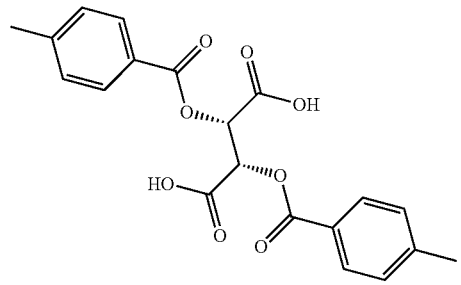

(I-11-A-R-D-Tol-Tart.)

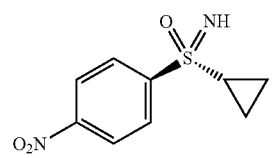

At 20° C., 116.4 g (301.2 mmol) of di-p-toluoyl-D-tartaric acid were added to a suspension of 64.9 g (286.8 mmol) of (I-11-A) in 1.3 l of acetonitrile and the mixture was stirred for 16 h at 20° C. The mixture was filtered with suction and the residue was washed twice with in each case 90 ml of acetonitrile. It was dried in vacuo at 40° C. to dryness, giving 71.1 g of (I-11-A-R-D-Tol-Tart.) This corresponded to a yield of 40.4%.

HPLC method A: retention time for (I-11-A-D-Tart): 9.6 min (36.2%) & 14.7 min (63.8%).

HPLC method B (L159-16EE): Chiralpak IC (DAICEL) length: 250 mm, internal diameter: 4.6 mm, particle size: 5 µm, gradient: 1:1 n-heptane/isopropanol isocratic; flow: 1.0 ml/min, detection at 252 nm, T=35° C.

Retention time for R enantiomer: 9.3 min; retention time for S enantiomer: 8.4 min; Enantiomer excess (ee): 99.6%.
MS (ES+): [M+H]$^+$=227; MS (ES−): [M−H]$^-$=385
$^1$H NMR (400 MHz, DMSO-d$_6$) δ ppm 0.91-1.06 (m, 3H) 1.10-1.20 (m, 1H) 2.41 (s, 6H) 2.72-2.84 (m, 1H) 4.64 (s, broad, 1H) 5.82 (s, 2H) 7.40 (d, J=8.07 Hz, 4H) 7.90 (d, J=8.07 Hz, 4H) 8.09-8.20 (m, 2H) 8.33-8.52 (m, 2H) 13.85 (s, broad, 2H).

Preparation of N—[(R)-cyclopropyl(4-nitrophenyl)oxido-lambda⁶-sulphanylidene]-2,2,2-trifluoroacetamide (I-3-A-R)

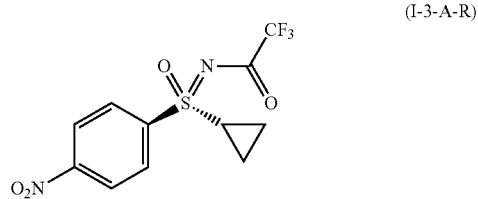

(I-3-A-R)

A solution of 72.1 g (117.7 mmol) of (I-11-A-R-D-Tol-Tart.) in 720 ml of dichloromethane was stirred for 60 min with a solution of 24.4 g of potassium carbonate in 350 ml of water at 20° C. The aqueous phase was extracted with 360 ml of dichloromethane and the combined organic phase was washed with 720 ml of water and dried over magnesium sulphate. The mixture was filtered and the filtrate was admixed with 49 ml (353.1 mmol) of triethylamine and then with 49.9 ml (353.1 mmol) of trifluoroacetic anhydride over the course of 40 min at 20-25° C. It was after-stirred for 10 min and then added to 1.1 l of a saturated sodium hydrogen carbonate solution. After separating the phases, washing with 1.0 l of water was carried out, followed by drying over magnesium sulphate, and the solvent was distilled off in vacuo. The residue was taken up in 120 ml of isopropanol and the resulting suspension was stirred for 1 hour at 0-5° C. It was filtered and the residue was washed twice with in each case 30 ml of cold isopropanol. It was dried in vacuo at 40° C., giving 27.3 g (75%) of (I-3-A-R.).

HPLC method A: retention time for (I-3-A-R): 16.4 min (99.6%).

HPLC method C (L159-10EE): Chiralpak IC (DAICEL) length: 250 mm, internal diameter: 4.6 mm, particle size: 5 µm, gradient: 1:1 n-heptane/ethanol isocratic; flow: 1.0 ml/min, detection at 240 nm, T=35° C.

Retention time for R enantiomer (I-3-A-R): 4.5 min; retention time for S enantiomer: 3.7 min; Enantiomer excess (ee): 100%.

MS (DCI): $[M+H]^+=323$, $[M+NH_4]^+=340$ $^1$H NMR (400 MHz, CHLOROFORM-d) δ ppm 1.11-1.29 (m, 1H) 1.36-1.52 (m, 2H) 1.74-1.88 (m, 1H) 2.69-2.89 (m, 1H) 8.14 (d, J=8.80 Hz, 2H) 8.47 (d, J=8.80 Hz, 2H).

Preparation of N—[(R)-(4-aminophenyl)(cyclopropyl)oxido-lambda⁶-sulphanylidene]-2,2,2-trifluoroacetamide (I-4-A-R)

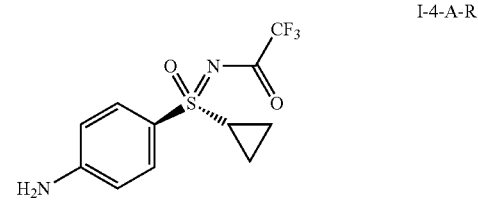

I-4-A-R

A suspension of 40.0 g (124.1 mmol) of (I-3-A-R) and 10.0 g of palladium on carbon (Pd/C: 5% Pd, 1% Fe, 55% water) in 800 ml of methanol was hydrogenated for seven hours at 2.5 bar. The mixture was filtered over kieselguhr and after-washed twice with in each case 200 ml of methanol. The filtrate was concentrated in vacuo and then 800 ml of water were added. The mixture was stirred for one hour, filtered and washed twice with in each case 400 ml of water. The crystals were dried in vacuo at 40° C. This gave 33.4 g (292.3 mmol) of the desired aniline (I-4-A-R). This corresponded to a yield of 92%.

HPLC method A: retention time for (I-4-A-R): 14.4 min (96.1%).

HPLC method C: retention time for R enantiomer (I-4-A-R): 13.7 min; retention time for S enantiomer: 12.2 min; enantiomer excess (ee): 100%.

MS (DCI): $[M+H]^+=293$, $[M+NH_4]^+=310$ $^1$H NMR (400 MHz, CHLOROFORM-d) δ ppm 1.00-1.16 (m, 1H) 1.17-1.40 (m, 2H) 1.56-1.71 (m, 1H) 2.74 (tt, J=7.79, 4.92 Hz, 1H) 4.33 (br. s., 2H) 6.67-6.79 (m, 2H) 7.58-7.74 (m, 2H).

Preparation of (4R,5R)-4,5-dimethyl-2-phenyl-1,3-dioxolane (I-12-A)

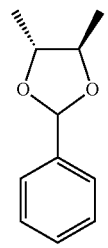

I-12-A

A solution of 300 g (3.33 mol) of 2R,3R-butanediol, 422 g (2.78 mol) of benzaldehyde dimethyl acetal and 7.0 g (27.7 mmol) of pyridinium p-toluenesulphonate in 1.2 l of toluene was heated to 50° C. At 600-800 mbar, ca. 400 ml of distillate were taken off over the course of 3 hours. It was cooled and the reaction mixture was added to 500 ml of a 1 M sodium hydroxide solution. The phases were separated and the organic phase was washed twice with in each case 500 ml of water. The organic phase was dried azeotropically, with ca. 250 ml of toluene being distilled off.

The product obtained in this way in toluene (1061 g) was used directly in the next stage. For the analysis, a part amount was evaporated to dryness.

The preparation of the compound (I-12-A) can inter alia also take place in accordance with the literature (Chemistry Letters (1995), 4, 263-4; Journal of Organic Chemistry (2003), 68(9), 3413-3415, Tetrahedron (1989), 45(2), 507-16; Journal of Organic Chemistry (2005), 70(20), 8009-8016; Bioorganic & Medicinal Chemistry Letters (2006), 16(1), 186-190; Journal of Organic Chemistry (1999), 64(20), 7594-7600).

GC method A: Column RTX-50 (fused silica, 100% methylphenylpolysiloxane)
length: 30 m, internal diameter: 0.32 mm, film thickness: 1.0 µm; flow: 3 ml/min; carrier gas hydrogen; detector FID 320° C., injector temperature 280° C.; analysis program: T=80° C., holding time 2 min, heating rate 10° C./min up to T=300° C., holding time 6 min.

Retention time (I-12-A): 12.1 min (98%), toluene 3.3 min.
MS (DCI): $[M+H]^+=179$ $^1$H NMR (400 MHz, CHLOROFORM-d) δ ppm 1.30-1.35 (m, 3H) 1.36-1.41 (m, 3H) 3.74-3.87 (m, 2H) 5.94 (s, 1H) 7.32-7.41 (m, 3H) 7.49 (dd, J=7.70, 1.83 Hz, 2H).

Preparation of (2R,3R)-3-(phenylmethoxy)-2-butanol (I-5-A)

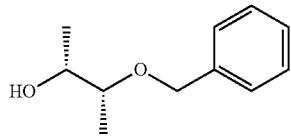

I-5-A

The toluenic solution of (I-12-A) obtained from the previous stage was divided and further reacted in two batches: 530 g of the (I-12-A) solution were diluted with 500 ml of toluene, heated to 55° C. and admixed over the course of one hour with 2.2 l of a 1.5 M diisobutylaluminium solution in toluene. The mixture was stirred for three hours at 50-60° C. The reaction mixture was added over the course of one hour at 20-25° C. to a suspension of 500 g of sodium sulphate decahydrate in 500 ml of toluene. Filtration was carried out, followed by after-washing ten times with in each case 500 ml of toluene. The combined organic phase was filtered over kieselguhr and the solvent was distilled off in vacuo. This gave 230 g (1.27 mol) of (I-5-A) in a partial conversion. This corresponded to a yield of ca. 76% over two stages.

The preparation of the compound (I-5-A) can inter alia also take place in accordance with the literature:
Bioorganic & Medicinal Chemistry Letters (2006), 16(1), 186-190; EP 1291336A2; Journal of the American Chemical Society (1997), 119(19), 4541-4542; Journal of Organic Chemistry (1990), 55(10), 3129-37.

HPLC method A: Retention time (I-5-A): 12.5 min (97.4%).

MS (EI+): [M+H]$^+$=181

$^1$H NMR (400 MHz, CHLOROFORM-d) δ ppm 1.16 (t, J=5.99 Hz, 6H) 2.77 (d, J=2.69 Hz, 1H) 3.25-3.36 (m, 1H) 3.61 (quind, J=6.54, 6.54, 6.54, 6.54, 2.69 Hz, 1H) 4.43 (d, J=11.49 Hz, 1H) 4.66 (d, J=11.49 Hz, 1H) 7.26-7.38 (m, 5H).

Preparation of 4-{[(2R,3R)-3-(benzyloxy)butan-2-yl]oxy}-2-chloro-5-(trifluoromethyl)-pyrimidine (I-7-A)

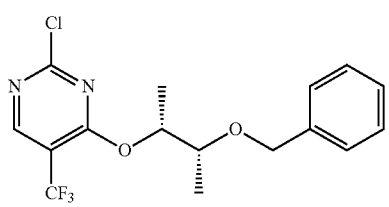

I-7-A

At −35° C. and over the course of 30 min, 680 ml of a 1 M lithium hexamethyl disilazide were metered into a solution of 140.4 g (647.3 mmol) of 2,4-dichloro-5-(trifluoromethyl)pyrimidine and 122.5 g (679.6 mmol) of (I-5-A) in 1.0 l of THF. The mixture was stirred for three hours at −30° C. It was heated to 0° C. and admixed with 1.0 l of water over the course of 15 min. 1.0 l of acetic ester was added, the phases were separated and the aqueous phase was extracted with 300 ml of acetic ester. The combined organic phase was concentrated by evaporation in vacuo to a volume of ca. 1.5 l and washed with 1.0 l of water. It was dried over sodium sulphate, filtered with suction over kieselguhr and evaporated in vacuo. This gave 238.4 g of the crude product as a brown oil. A second batch on the same scale produced a further 236 g of crude product.

Both batches were combined and dissolved in 470 ml of heptane/acetic ester 1:1. The mixture was filtered with suction over silica gel 60 and washed twice with in each case 1.0 l of acetic ester. The combined filtrates were filtered over kieselguhr and dried over magnesium sulphate, and the solvents were distilled off in vacuo. The residue was chromatographed over 15 kg of silica gel 60 with n-heptane/acetic ester 15:1. This gave 171 g of (I-7-A) (35%) and 63 g of a mixed fraction which still contained 58 area % (I-7-A).

HPLC method A: Retention time (I-7-A) (4-isomer) 21.6 min (95%); retention time of the 2-isomer: 21.0 min

MS (ES−API): [M+H]$^+$=361

$^1$H NMR (400 MHz, DMSO-d$_6$) δ ppm 1.16 (d, J=6.36 Hz, 3H) 1.32 (d, J=6.36 Hz, 3H) 3.74 (quin, J=6.17 Hz, 1H) 4.46 (d, J=11.98 Hz, 1H) 4.61 (d, J=11.98 Hz, 1H) 5.44 (quin, J=6.24 Hz, 1H) 7.11-7.46 (m, 5H) 8.85 (s, 1H).

Preparation of N-[(4-{[4-{[(2R,3R)-3-(benzyloxy)butan-2-yl]oxy}-5-(trifluoromethyl)pyrimidin-2-yl]amino}phenyl)(cyclopropyl)oxido-lambda$^6$-sulphanylidene]-2,2,2-trifluoroacetamide benzenesulphonic acid salt (1:1) (I-8-A-R-BSA)

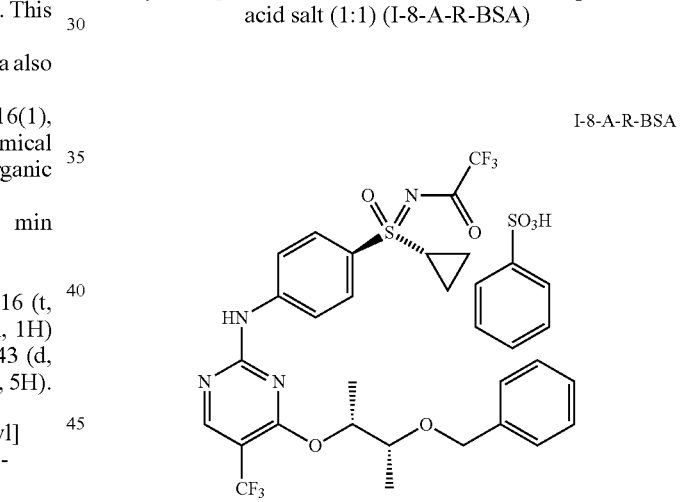

I-8-A-R-BSA

A suspension of 52.0 g (144 mmol) of (I-7-A), 42.1 g (144 mmol) of (I-4-A-R) and 22.8 g (144 mmol) of benzenesulphonic acid in 842 ml of dioxane was stirred for 16 h at 20° C. The mixture was then heated at 55-60° C. for 19 hours. For the isolation, it was admixed at 20° C. with seed crystals and diluted with 1.68 l of n-heptane. It was stirred for one hour, filtered with suction, washed with 240 ml of dioxane/n-heptane (1:1) and with 240 ml of n-heptane. It was dried to constant weight in vacuo at 40° C. This gave 113.7 g (100%) of the desired product as beige crystals.

HPLC method A: Retention time (I-8-A-R-BSA) 22.3 min (94%); retention time for the already partially deprotected trifluoroacetate cleavage product 19.1 min (2.4%).

MS (ES$^+$): [M+H]$^+$=617

$^1$H NMR (500 MHz, DMSO-d$_6$) δ ppm 1.10 (m, 2H) 1.19 (m, 3H) 1.34 (m, 3H), 1.45 (m, 1H) 3.38 (m, 1H) 3.77 (m, 1H) 4.49 (d, 1H) 4.60 (d, 1H) 5.52 (m, 1H) 7.30 (m, 7H) 7.60 (m, 2H) 7.92 (m, 2H) 8.09 (m, 2H) 8.63 (m, 1H) 10.71 (m, 1H).

Preparation of (2R,3R)-3-{[2-{[4-(S-cyclopropylsul-phonimidoyl)phenyl]amino}-5-(trifluoromethyl)pyrimidin-4-yl]oxy}butan-2-ol (Compound A)

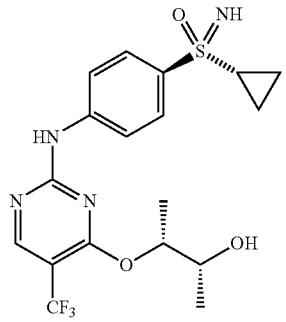

Compound A

Hydrogen was bubbled through a suspension of 120 g of (I-8-A-R-BSA) and 60 g of 10% Pd/C in 640 g of methanol for 6 h at atmospheric pressure. Washing was carried out over kieselguhr and twice with in each case 100 g of methanol. 53 g of potassium carbonate were added to the filtrate and the mixture was stirred for 1 h at 20° C.

For the work-up, 900 g of water and 700 g of dichloromethane were added. The aqueous phase was extracted with 700 g of dichloromethane and the combined organic phases were washed with 900 g of water and dried over sodium sulphate. Filtration was carried out, followed by after-washing with 400 g of dichloromethane. The solvent was distilled off in vacuo. The residue was dissolved in 10 g of acetic ester and admixed with 125 g of n-heptane. The mixture was stirred for 10 min at 20° C. and admixed again with 125 of n-heptane. The following were carried out, stirring for two hours at 20° C., filtration, washing with a mixture of n-heptane (70 g)/acetic ester (45 g) and with 100 g of n-heptane. Drying was carried out in vacuo at 30° C. to constant mass. This gave 47 g (69%) of the target compound.

HPLC method A: Retention time compound A 14.24 min (100%).

MS (ESI$^+$): [M+H]$^+$=431

$^1$H NMR (500 MHz, DMSO-d$_6$) δ ppm 0.92 (m, 3H) 1.10 (m, 4H) 1.30 (d, 3H) 2.62 (m, 1H) 3.85 (m, 1H) 4.08 (s, 1H) 4.91 (d, 1H) 5.31 (m, 1H) 7.83 (d, 2H) 7.94 (d, 2H) 8.59 (s, 1H) 10.50 (m, 1H).

The invention claimed is:

1. A process for the preparation of a compound of the general formula (I)

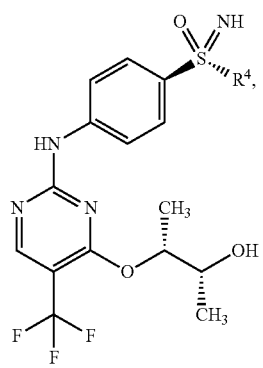

(I)

in which
R$^4$ is a C$_1$-C$_6$-alkyl group or a C$_3$-C$_7$-cycloalkyl ring, comprising:

cleaving of the protective groups of a benzenesulphonic acid salt of a doubly protected anilinopyrimidine of the formula (I-8-R-BSA)

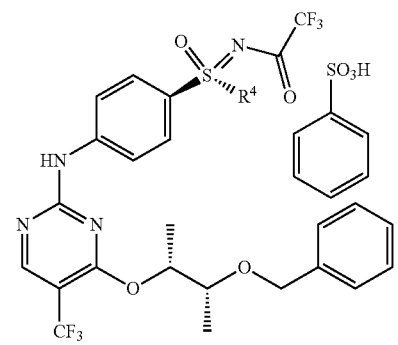

I-8-R-BSA by hydrogenation with palladium on activated carbon and hydrogen in methanol, and also by treatment with potassium carbonate in methanol to give a compound of formula (I).

2. The process according to claim 1, comprising benzenesulphonic acid-catalysed coupling of a compound of formula (I-7-A)

I-7-A

[Structure of I-7-A]

and a compound of formula (I-4-R)

I-4-R

[Structure of I-4-R]

to prepare the benzenesulphonic acid salt of a doubly protected anilino-pyrimidines of formula (I-8-R-BSA).

3. The process according to claim 2, comprising coupling a compound of formula (I-5-A)

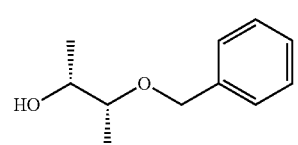

I-5-A with 2,4-dichloro-5-trifluoromethylpyrimidine in a lithium base and ethereal solvent to prepare the compound of formula (I-7-A).

4. The process according to claim 3, comprising reacting benzaldehyde dimethyl acetal with (2R,3R)-butane-2,3-diol in the presence of pyridinium p-toluenesulphonate in toluene to provide (4R,5R)-4,5-dimethyl-2-phenyl-1,3-dioxolane, and reducing the (4R,5R)-4,5-dimethyl-2-phenyl-1,3-dioxolane with diisobutylaluminium hydride in toluene to provide the compound of formula (I-5-A).

5. The process according to claim 2, comprising hydrogenating a compound of formula (I-3-R)

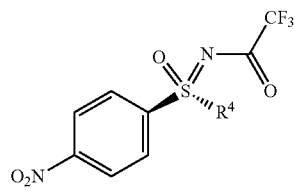

I-3-R with an iron-doped palladium catalyst to provide a compound of formula (I-4-R).

6. The process according to claim 5, wherein the hydrogenation is performed in a solvent selected from methanol, ethanol, isopropanol, tetrahydrofuran, and acetic acid.

7. The process according to claim 5, comprising racemate cleavage of a compound of formula (I-11)

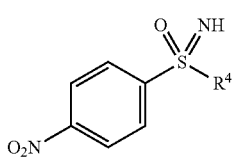

I-11 (rac.)

using (+)-di-O-p-toluoyl-D-tartaric acid to give an intermediate salt of formula (I-11-R-D-Tol-Tart)

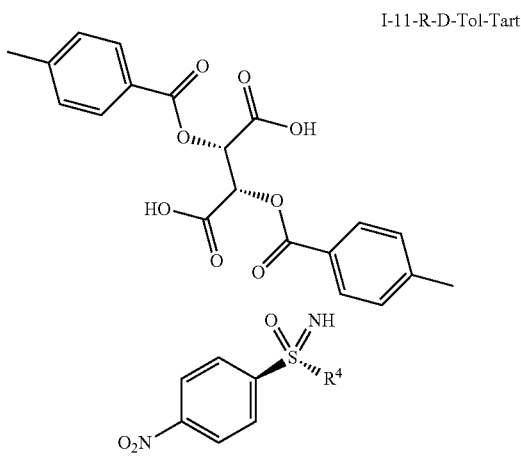

I-11-R-D-Tol-Tart and the release of a compound of formula (I-11-R)

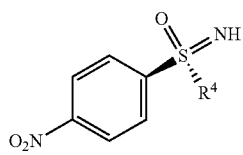

I-11-R from the salt and the insertion of a trifluoroacetate protective group to form the compound of formula (I-3-R).

8. The process according of claim 7, wherein the cleavage is performed in acetonitrile or propionitrile.

9. The process according of claim 7, comprising oxidation of a compound of formula (I-10)

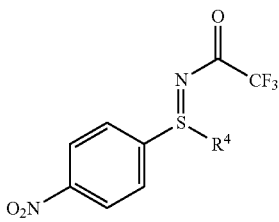

I-10 to give a compound of formula (I-3)

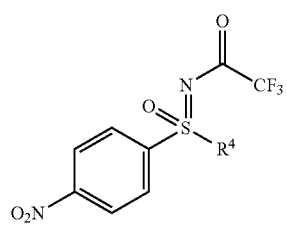

I-3 and subsequent deprotection to give the compound of formula (I-11).

10. The process according to claim 9, wherein the oxidation step takes place with potassium peroxomonosulphate.

11. The process according to claim 9, comprising oxidative amination of a compound of formula (I-1)

I-1 by an oxidizing agent in a base to give the compound of the formula (I-10).

12. The process according to claim 11, wherein the oxidizing agent is selected from N-bromosuccinimide, iodine, sodium hypobromide, 1,3-dibromo-5,5-dimethylhydantoin, N-chlorosuccinimide and trichlorocyanuric acid; and the base is selected from potassium tert-butylate, aqueous sodium hydroxide solution, sodium methanolate, sodium ethanolate, and sodium hydride.

13. The process according to claim 11, comprising alkylating 4-nitrothiophenol using the compound $$X\text{—}R^4$$

where X is Br, Cl, I, O—SO$_2$—CH$_3$ or O—SO$_2$-(4-methylphenyl), in the presence of potassium carbonate in N-methylpyrrolidinone to give the compound of formula (I-1).

14. The process according to claim 11,
wherein the oxidizing agent is 1,3-dibromo-5,5-dimethylhydantoin in trifluoroacetamide.

15. The process according to claim 3,
wherein the lithium base is selected from lithium hexamethyldisilazide, n-butyllithium, lithium diisopropylamide, and lithium-2,2,6,6-tetramethylpiperidine; and the ethereal solvent is selected from tetrahydrofuran, 1,2-dimethoxyethane, 1,4-dioxane, methyl tert-butyl ether, diisopropyl ether, n-dibutyl ether, 2-methyltetrahydrofuran, and cyclopentyl methyl ether.

16. A salt of the formula (I-11-R-D-Tol-Tart)

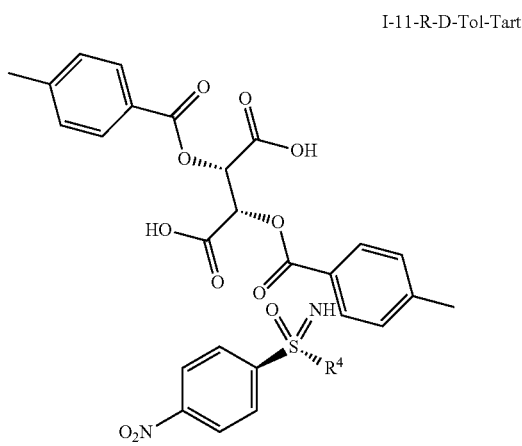

I-11-R-D-Tol-Tart where $R^4$ is a $C_1$-$C_6$-alkyl group or a $C_3$-$C_7$-cycloalkyl ring.

17. A salt of the formula (I-8-R-BSA)

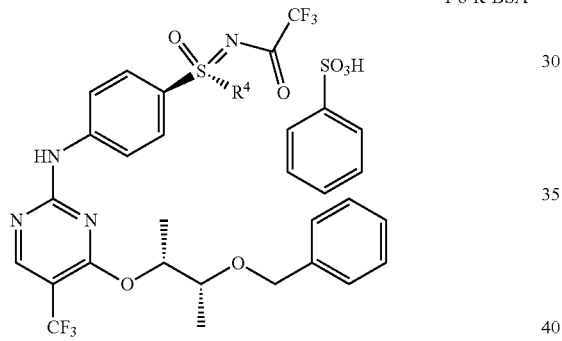

I-8-R-BSA where $R^4$ is a $C_1$-$C_6$-alkyl group or a $C_3$-$C_7$-cycloalkyl ring.

18. The salt according to claim 16, which is

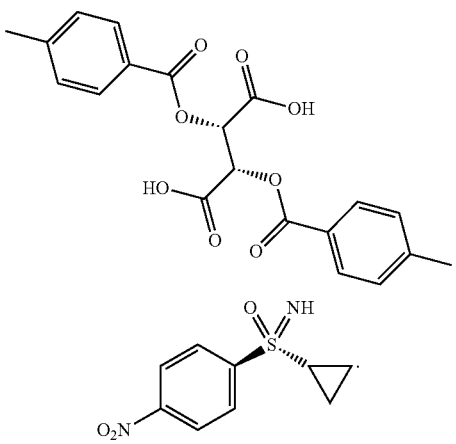

I-11-R-D-Tol-Tart

19. The salt according to claim 17, which is

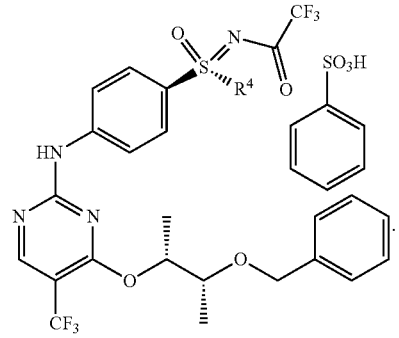

I-8-R-BSA

* * * * *